US006100382A

United States Patent [19]
Wolfe et al.

[11] Patent Number: 6,100,382

[45] Date of Patent: Aug. 8, 2000

[54] METHOD AND COMPOSITION FOR REMEDIATING ENVIRONMENTAL CONTAMINANTS

[75] Inventors: N. Lee Wolfe, Athens; Laura H. Carreira, Danielsville; Mark C. Delgado, Athens, all of Ga.

[73] Assignees: The United States of America as represented by the Environmental Protection Agency, Washington, D.C.; Dyncorp, Inc, Reston, Va.

[21] Appl. No.: 08/897,203

[22] Filed: Jul. 21, 1997

Related U.S. Application Data

[62] Division of application No. 08/632,884, Apr. 16, 1996, Pat. No. 5,711,020, which is a continuation of application No. 08/447,483, May 23, 1995, abandoned, which is a division of application No. 08/045,966, Apr. 9, 1993, abandoned.

[51] Int. Cl.$^7$ .................................................. C07K 15/00
[52] U.S. Cl. ...................... 530/370; 530/412; 435/262.5; 424/195.1
[58] Field of Search ...................................... 530/370, 412; 435/262.5; 424/195.1

[56] References Cited

U.S. PATENT DOCUMENTS 4,695,550  9/1987  Mans ........................................ 435/194

OTHER PUBLICATIONS

Andersson et al., *Int. Union Crystallogr.*, Crystollagr. Symp., 5(Crystrallogr. Comput. 5), 20–8, 1991.
Vaughn et al., *Protoplasma*, 156 (3), 117–29, 1990.
Gardner et al., *Biochemistry*, vol. 15, No. 3, pp. 688–697, 1976.
Rothe et al., *Electrophoresis*, 3, pp. 43–48, 1982.
Adhya T.K. et, al. *J. Agric. Food Chem.* 29:90–93 (1981).
Alvarez, M. et al., "Enzyme Catalyzed Transformation of 2, 46–Trinitrotoluene", Abstracts of the General Meeting of the Am. Soci. for Microbiology, 91:217 (1991).
Anastos, G.J. et. al. "Innovative Technologies for Hazardous Waste Treatment", Nuclear and Chemical Waste Management, vol. 8, pp. 269–281 (1988).
Araujo, R. and Molina, M., "Inhibition of Acclimation by Competition, Alternative Substrates and Low Concentration of Chemical", Abstracts of the General Meeting of the Am. Soc. for Microbiology, vol. 91, pp. 303 (1991).
Bolton, H., Jr., et. al., "Effect of Chemical Speciation on the Degradation of NTA by a Psuedomonas sp." Abstracts of the General Meeting of the Am. Soci. for Microbiology, vol. 91, pp. 304, (1991).
Camper, N.D., et al., J.Environ Sci. Health, B15; 457–473 (1980).
Carreira, L. H. et al., "Isolation and characterization of a sediment component that reduces 2,4,6–trinitrotoluene", 203rd Am. Chem. Soc. Nat. Meeting and Exposition, (Apr. 5–10, 1992).
Donberg, P.A., "The Biodegradation of Acrylonitrile in Soil", Abstracts of the General Meeting of the Am. Soc. for Microbiology, vol. 91, pp. 304 (1991).

Golab, T., et al., "Fate of [$^{14}$C]Trifluralin in Soil" J. Agric. Food Chem., vol. 27, pp. 163–179 (1979).
Golab, et al., "Fate of Benefin in Soils, Plants, Artificial Rumen Fluid, and the Ruminant Animal", J. Agric. Food Chem., vol. 18, pp. 838–844 (1970).
Graetz, D.A., et al., "Parathion Degradation in Lake Sediments", J. Water, Poll. Control Fed., vol. 42, pp. R76–94 (1970).
Haigler, B.E. et al., "Degradation of Nitrobenzene by Bacteria Containing Toluene Degradative Pathways" Abstracts of the General Meeting of the Am. Soc. for Microbiology, vol. 91, pp. 303 (1991).
Hanne, L.F., et al., "Characterization of Soil Actinomycetes Capable of Degrading para–Nitrophenol" Abstracts of the General Meeting of the Am. Soc. for Microbiology, vol. 91, pp. 303 (1991).
Harper, D.B., "Microbial Metabolism of Aromatic Nitriles", Biochem, J., vol. 167, pp. 685–692 (1977).
Kaufman, D.D., "Degradation of Pesticides by Soil Microorganisms", Pestic, in Soil and Water, pp. 103–233 (1974).
Kulpa, C. et al., "Degradation of Trinitrotoluene by a Mixed Microbial Culture Isolated from Soil", Abstracts of the General Meeting of the Am. Soc. for Microbiology, vol. 91, pp. 303 (1991).
Lee, C.M. et al., Inter. J. Environ, Anal. Chem., vol. 35, pp. 49–225 (1989).
Murthy, N.B.K. et al., "Degradation of Pentachloronitobenzene (PCNB) in Anaeorobic Soils", J. Agric. Food Chem., vol. 26, pp. 1151–1156 (1978).
Nishino, S.F. et al., "Initial Steps in the Bacterial Degradatio nof 2,4–Dinitrotoluene", Abstracts of the General Meeting of the Am. Soc. of Microbiology, vol., 91, pp. 303 (1991).
Probst, G.W., et al., "Fate of Trifluralin in Soils and Plants", J. Agric. Food chem., vol. 15, pp. 592–599 (1967).
T.–Y. Ou, et atl., "Nitroreduction of 2,4,6–trinitrotoluene (TNT) in contaminated soils", Am. Chem. Soc. Nat. Meeting and Exposition, (Apr. 5–10, 1992).
Rickard, R.W. et al., "Degradation of Fluometuron by Rhizoctonia solani", Env. Health and Pollution Control, vol. 15.10, pp. 458 (1980).
Roberts, D.J. et al., "Anaerobic Degradation of TNT", Abstracts of the General Meeting of the Am. Soc. for Microbiology, vol. 91, pp. 303 (1991).

(List continued on next page.)

*Primary Examiner*—Dwayne C. Jones
*Assistant Examiner*—C. Delacroix-Muirheid
*Attorney, Agent, or Firm*—Jones & Askew

[57] ABSTRACT

A method and composition for the remediation of environmental contaminants in soil, sediment, aquifer material or water wherein contaminants are first reduced with a reducing agent found in sediment and are then oxidized to environmentally safe products. The composition includes a reducing agent, solubilized from sediment by a solvent, for reduction of environmental contaminants such as nitroorganics, halogenated hydrocarbons, cyano compounds, anisoles and metals.

10 Claims, 12 Drawing Sheets

OTHER PUBLICATIONS

Wahid, P.A. et al., "Instantaneous Degradation of Parathion in Anaerobic Soils", J. Environ. Qual., vol. 9, pp. 127–130 (1980).

Williams, P.P., "Metabolism of Synthetic Organic Pesticides by Anaerobic Microorganisms", Residue Rev., vol. 66, pp. 63–135 (1977).

Williams, R.T., "Composting of Explosives Contaminated Sediments", Abstracts of the General Meeting of the Am. Soc. for Microbiology, vol. 91, pp. 302 (1991).

Willis, G.H., et al., "Degradation of Trifluralin in Soil Suspensions as Related to Redox Potential", J. Environ. Qual., vol. 3, pp. 262–265 (1974).

Schedule for the 203rd Am. Chem. Soc. Nat. Meeting and Exposition (Apr. 5–10, 1992).

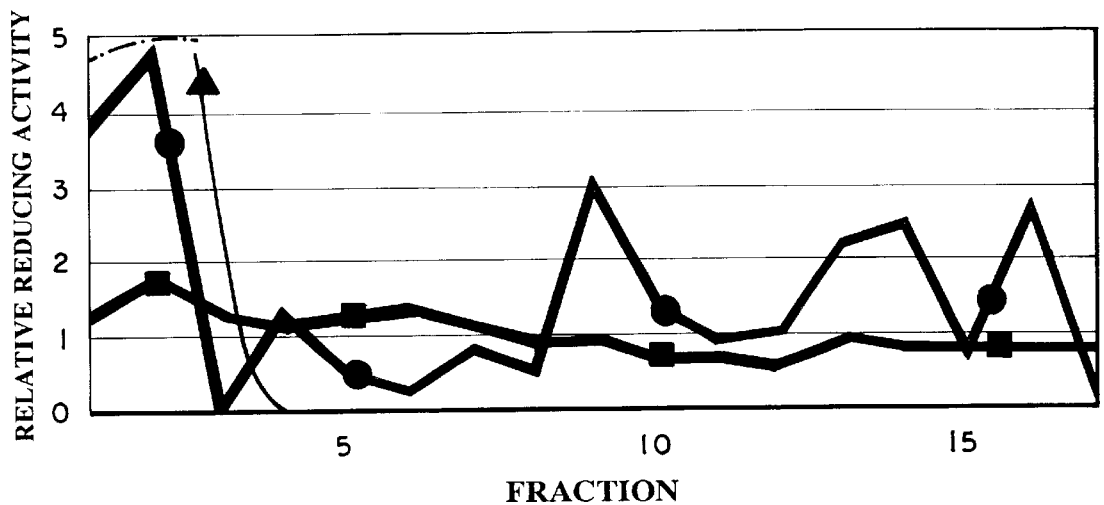
Fig_1
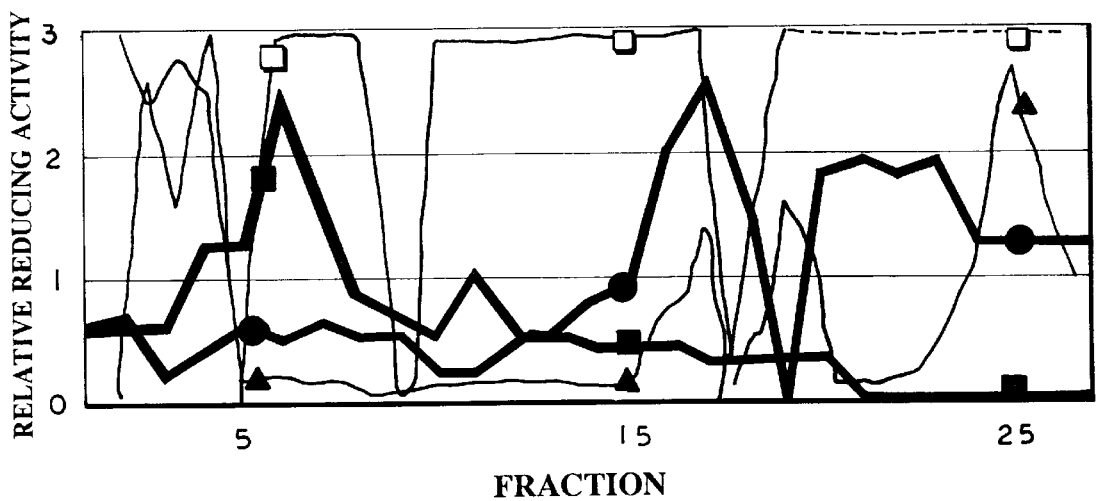
Fig_2

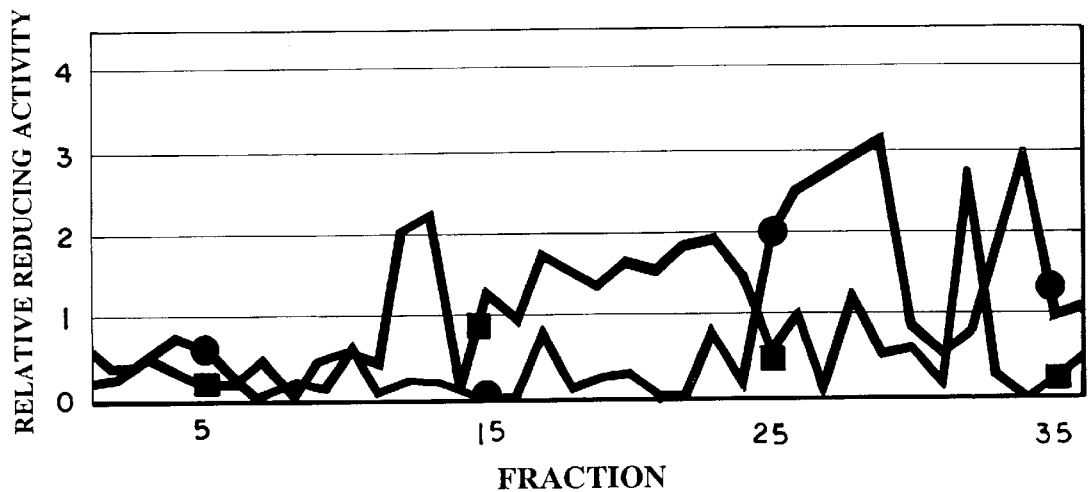
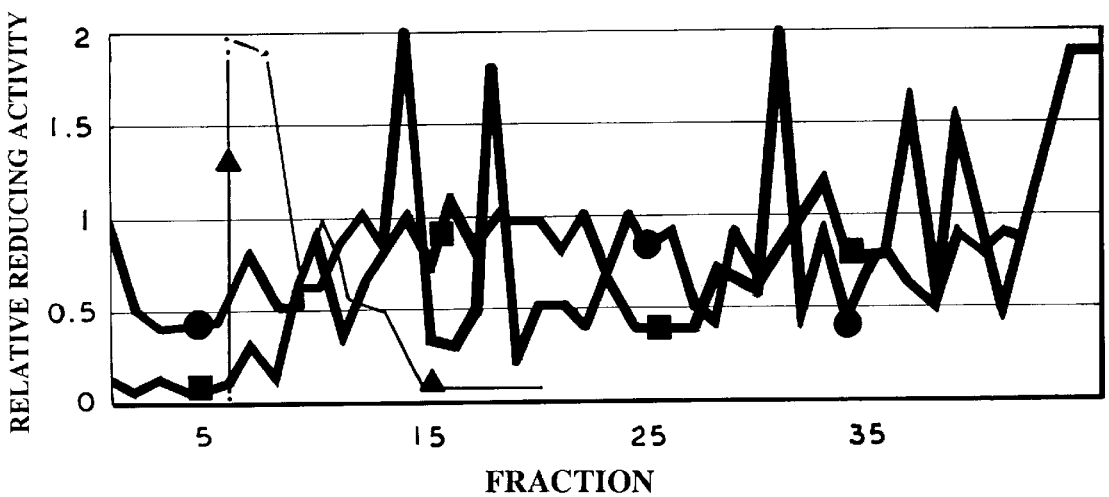

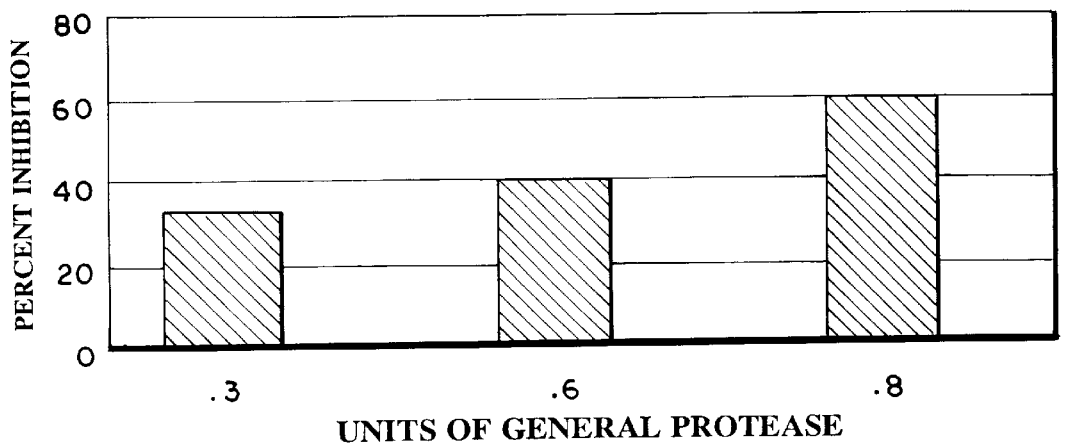
Fig_5
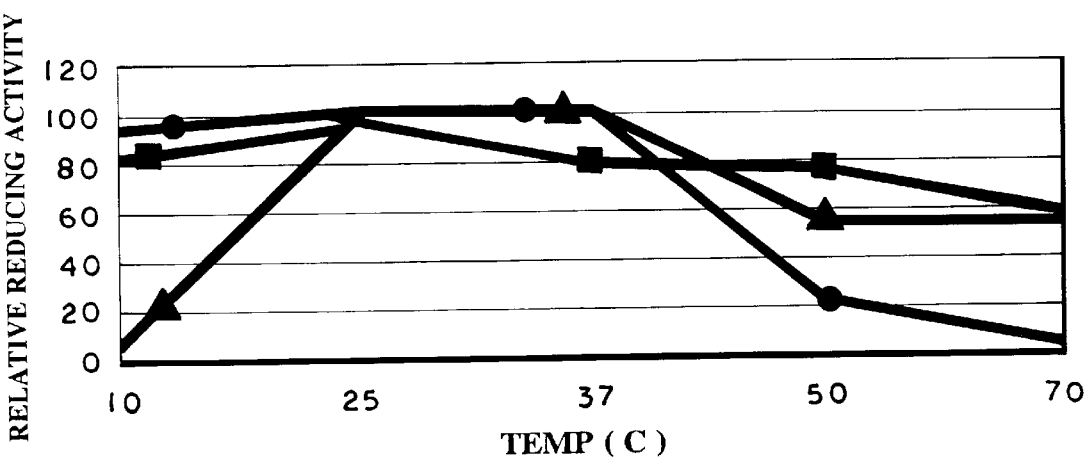
Fig_6

Fig. 7
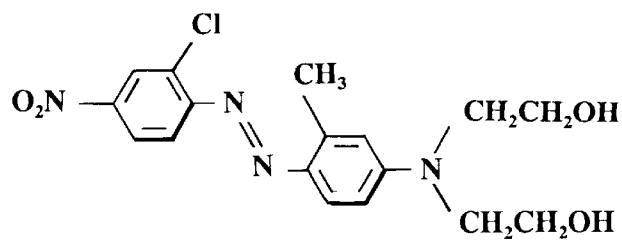
DISPERSE RED 5
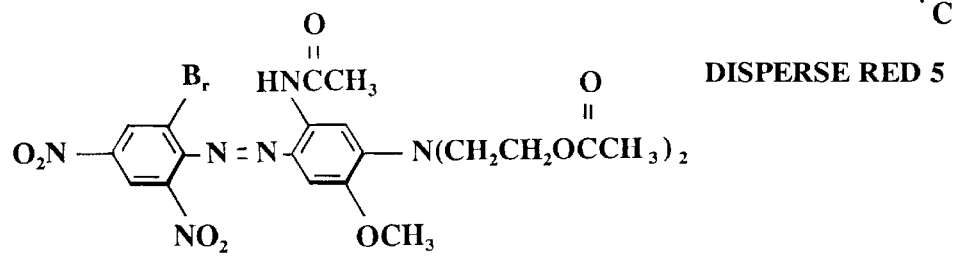
DISPERSE BLUE 79
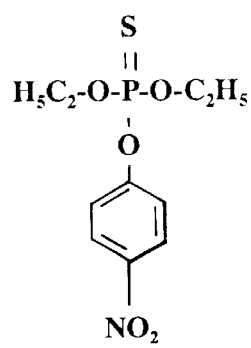
PARATHION
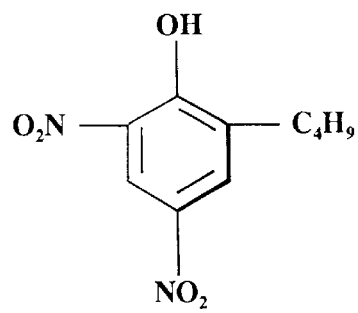
DINOSEB
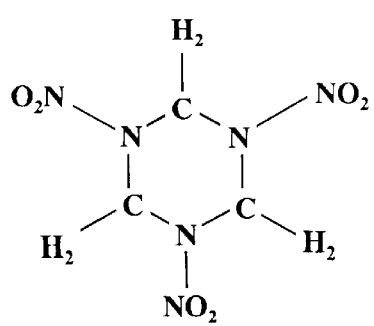
RDX
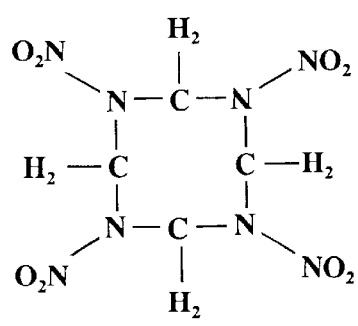
HMX
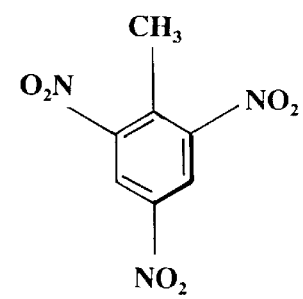
TNT

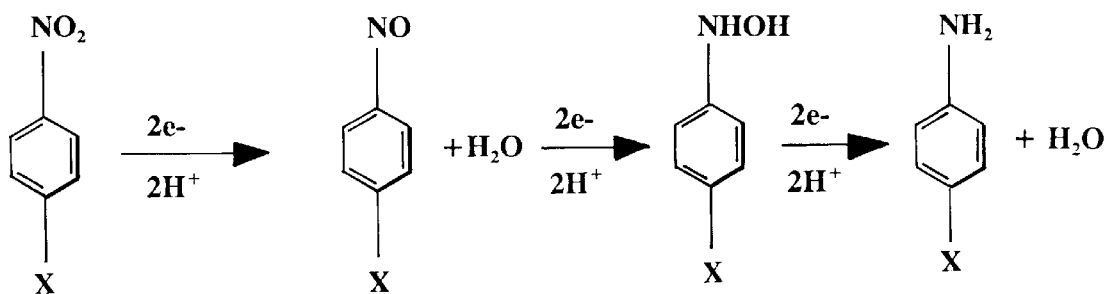
X = NITRO, ACETYL, CYANO, CHLORO, BROMO, HYDROGEN, METHOXY, ETHYL, N-BUTYL, N-OCTYL, E⁺ -, AND METHYL
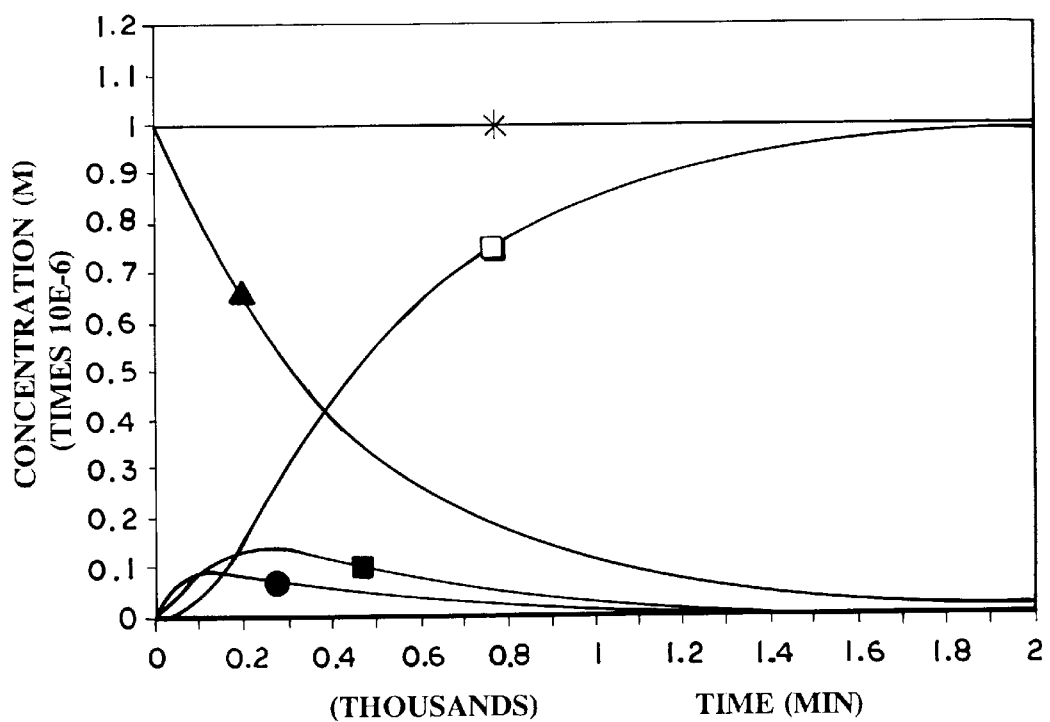

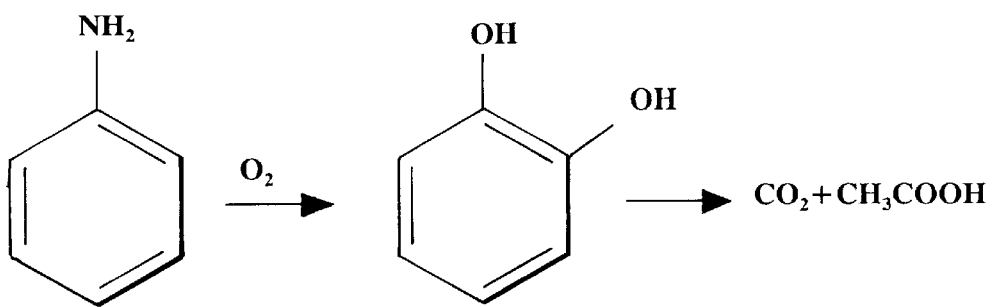
Fig_10
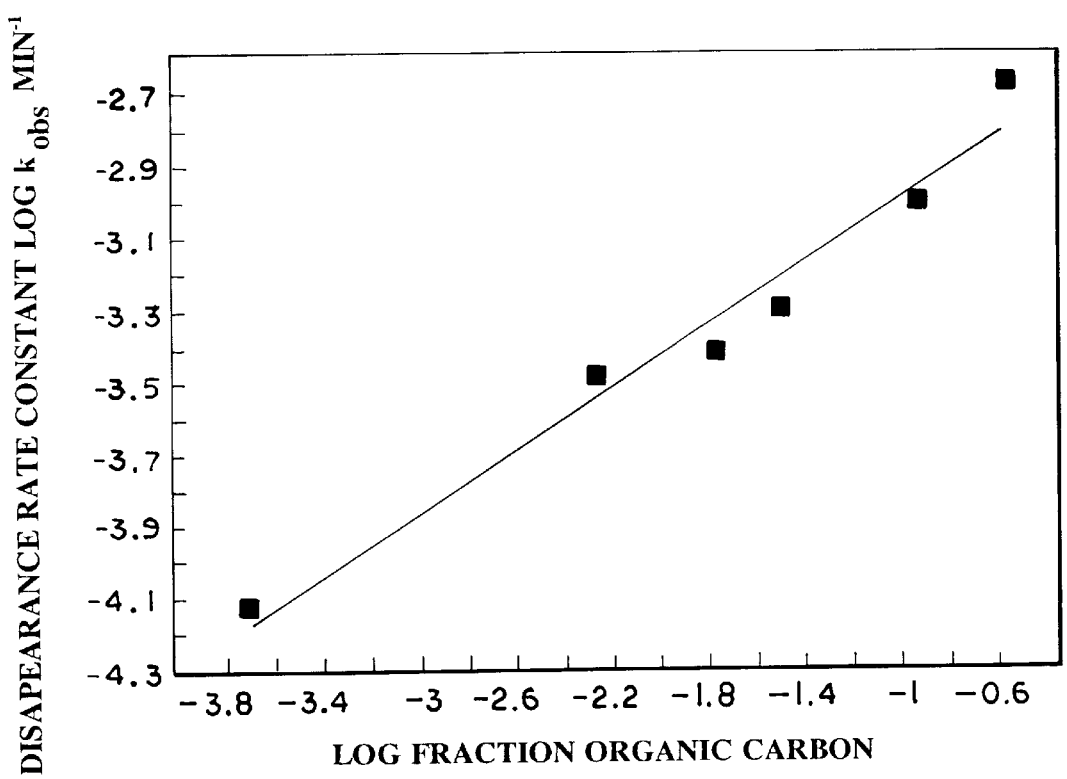
Fig_11

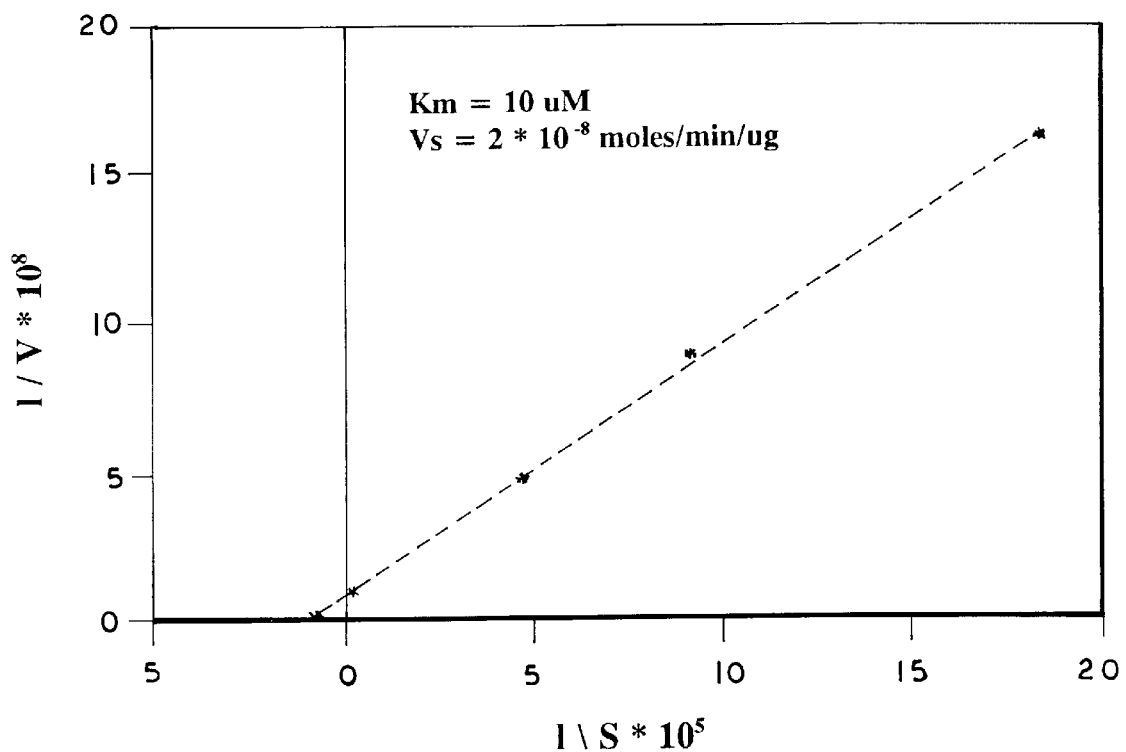
Fig_21

METHOD AND COMPOSITION FOR REMEDIATING ENVIRONMENTAL CONTAMINANTS

This is a division of application Ser. No. 08/632,884 filed Apr. 16, 1996, now U.S. Pat. No. 5,711,020, which is a continuation of application Ser. No. 08/447,483, filed May 23, 1995, now abandoned, which is a division of application Ser. No. 08/045,966 filed Apr. 9, 1993, now abandoned.

BACKGROUND OF THE INVENTION

The present invention relates to the field of ecology and more particularly to the remediation of environmental contaminants by enzymatic reduction and oxidation.

Contamination of the air, water and soil is a severe problem endangering the lives of many plants and animals, including humans. Many attempts have been made to reduce contamination by either preventing escape of the contaminants into the environment, containing the contaminants at one site, or treating the contaminants in some way to make them less harmful.

Extensive soil, water, sediment and aquifer contamination has occurred from the manufacture and widespread use of explosives by both civilians and the military. For example, the compound 2,4,6-trinitrotoluene (TNT) is a highly oxidized nitroaromatic that is stable on soil surfaces in the environment for as many as 40 years.

Currently, the preferred technology for remediating TNT-contaminated soil is by burning the soil and then cashing the incinerated soil in an enclosure for an indefinite amount of time. The burning treatment is expensive, costing $300–400 per ton, and, for a large contaminated site encompassing several acres, could cost tens of millions of dollars.

Scientists have shown that it is possible to degrade certain organic pollutants in soil through oxidation/reduction (redox) reactions. The goal has been to chemically or biologically oxidize or reduce the contaminants or functional moieties of the contaminants to innocuous compounds or compounds that can be easily degraded and eliminated from the soil by known processes.

Nitroorganic Pesticides

Environmental contaminants that have been partially degraded through redox reactions include nitroaromatic pesticides such as parathion, methyl parathion, trifluralin, profluralin, benefin, nitrofen and pentachloro-nitrobenzene as described by Williams, P. P., *Residue Rev.* 66:63–135 (1977); Wahid, P. A. et al., *J. Environ. Qual.* 9:127–130 (1980); Graetz, D. A. et al., *J. Water Poll. Control Fed.* 42:R76–R94 (1970); Adhya, T. K. et al., *J. Agric. Food Chem.* 29:90–93 (1981); Camper, N. D. et al., *J. Environ. Sci. Health* B15:457–473 (1980); Golab, T. et al, *J. Agric. Food Chem.* 27:163–179 (1979); Probst, G. W. et al., *J. Agric. Food Chem.* 15:592–599 (1967); Willis, G. H. et al., *J. Environ. Qual.* 3:262–265 (1974); Golab. T. et al., *J. Agric. Food Chem.* 18:838–844 (1970); Lee, J. K. et al., *Misaengmul Hakhoe Chi.* 20:53–66 (1982); Qian, W. W. et al., *Huanjing Kexue* 3:36–39 (1982); and Murthy, N. B. K. and D. D. Kaufman, *J. Agric. Food Chem.* 26:1151–1156 (1978).

These nitroaromatic pesticide treatments generally involve the anaerobic transformation of the pesticides to reduced compounds by unidentified substances naturally present in the soil. However, the reduced products of nitroaromatic pesticide degradation include anilines and other compounds that are considered to be environmental hazards.

Nitroorganic Explosives

Many unsuccessful attempts have been made to oxidize the explosives 2,4,6, -trinitrotoluene (TNT), hexahydro-1,3,5-trinitro-1,3,5-triazine (RDX), octahydro-1,3,5,7-tetranitro-1,3,5,7-tetraazocine (HMX) and N-methyl-N-2,4,6-tetranitroaniline (Tetryl), nitrocellulose and red water (a by-product of TNT production) to innocuous products. None have found any practical or commercial application because these compounds are highly oxidized, and further oxidation generally requires excessive amounts of energy. Attempts have also been made to remediate these compounds microbially by reduction under anaerobic conditions. (Alvarez, M. et al., Enzyme Catalyed Transformation of 2,4,6-Trinitrotoluene, *Abstracts of the General Meeting of the Am. Soc. for Microbiology* 91:217 (1991)) However, the reduction products of these compounds include the corresponding amines and several other less well defined hydroxyazo compounds. The analogs of these reduction products are potential carcinogens and are considered to be environmentally hazardous.

Halogenated Hydrocarbons

Halogenated hydrocarbons as a class of compounds are one of the most ubiquitous pollutants in the United States. They have been and still are widely used in many industries as cleaning solvents, refrigerants, fumigants and starting materials for the syntheses of other chemicals. Because of their extensive use, there are hundreds of contaminated groundwater and landfill sites in the United States, many of which are superfund sites for which there is no inexpensive, effective remediation technology available. Also, industrial waste treatment technology is expensive and not always effective.

In contaminated ground water systems, the water is pumped out of the reservoir and treated with the "air stripping" treatment procedure. Halogenated hydrocarbons have also been remediated by a photolysis procedure wherein contaminated soil or sediment is placed on an oxide film and irradiated with concentrated sunlight to remove chloride atoms. These procedures are expensive and only successful if all of the contaminated material has been successfully removed from the site of contamination. Effective in situ treatment is not practiced because of a lack of treatment technology. Bioremediation has not been successful because maintenance of a viable microorganism population is not generally feasible in subsurface ecosystems. Chemical remediation processes have not been utilized because of the delivery of large amounts of the necessary chemicals and problems associated with groundwater hydrology.

Bioremediation has received considerable attention as an in situ remediation process of contaminated waste sites. The parent pollutants, however, are often resistant to degradation and must first be transformed to more degradable compounds for the processes to be effective. Although many microorganisms have been isolated that are capable of degrading halogenated hydrocarbons in the laboratory, they are not always effective when ported to the field situation.

Cyano Compounds

Aliphatic and aromatic cyano compounds are used as solvents and intermediates in the chemical industry in a variety of synthetic processes including textiles and pesticides. For example, acrylonitrile is a high production compound with output exceeding more than 2.3 billion pounds a year. These compounds can enter the environment through manufacturing waste waters and from the polymers of which they are associated and as a result of applications of pesticides such as dichlobneil (2,6-dichlorobenzonitrile) and bromoxynil (3,5-dibromo-4-hydroxybenzonitrile).

Biodegradation of selected cyano compounds has been demonstrated in waste water treatment systems. In soils, however, degradation is more difficult and high concentrations of the pollutants are often not readily degraded. Also, not all soils, in particular sandy soils, have the necessary microbial populations to degrade nitrites.

Anisoles

Anisoles are used as intermediates in the chemical industry for the manufacture of a large number of polymer, dye and pesticide compounds. These compounds find their way into the environment through point source and non-point source pathways. For example, the pesticide methoxyclor has been one of the most widely used pesticides in the United States. In general, anisoles are hard to degrade because the methyl-oxygen bond is very strong.

Other Contaminants

Remediation of other environmental contaminants such as metals has also been largely unsuccessful. Metal contaminants have been treated by the "pump and treat" procedure wherein water is pumped out of the contaminated area and passed over a tube containing titanium to transform the contaminants to compounds that are less hazardous to the environment. The "pump and treat" method is very costly, is only applicable for removal of volatile contaminates from surface water or aquifers, and is not successful until the source of the contamination is depleted.

It would be of great environmental benefit to have an inexpensive method of degrading contaminants in soils, waters, sediments, and aquifer materials that results in products that are environmentally acceptable.

It is therefore an object of the present invention to provide an improved method of remediating environmental contaminants.

It is a further object of the present invention to provide a method of remediating environmental contaminants that can be carried out in situ and in batch reactors.

It is a further object of the present invention to provide a composition for rapid reduction of contaminants.

It is a further object of the present invention to provide a process for the production of contaminant-reducing agents from soil.

It is a further object of the present invention to provide a method of remediating nitro-, halogenated-, cyano-, methoxy-organic, and metal contaminants from the environment.

It is a further object of the present invention to provide a method of oxidizing reduced pollutants.

It is a further object of the present invention to provide a method of remediating environmental contaminants that is cost-effective.

It is a further object of the present invention to provide a method of remediating soils, sediments, and aquifers that maintains the integrity of the environmental compartment.

SUMMARY OF THE INVENTION

A method for the remediation of contaminants of soil, water, sediment and aquifers is disclosed wherein contaminants are first reduced by a reducing agent found in soil and sediment having a substantially high organic content and are then oxidized to environmentally safe products. Reduction preferably takes place in a substantially anaerobic environment. An anaerobic environment is naturally present in water and aquifers and can be created in contaminated soil or sediment by flooding the soil or sediment with water.

Reduction of contaminants is achieved by combining the contaminated soil, water, sediment or aquifer material with either soil containing an adequate amount of the reducing agent, a crude enzyme preparation containing the reducing agent, the reducing agent as a semi-purified or purified enzyme specific for reduction of a particular contaminant, or a combination thereof. The contaminated soil, water, sediment or aquifer material is incubated with the reducing agent for a sufficient amount of time to allow reduction of the contaminants. The addition of a reducing metal, such as iron, to the soil further accelerates the remediation process.

Oxidation is achieved by oxygenating the water, aquifer material, flooded soil, or sediment containing the reduced contaminant or by simply removing the water from flooded soil or sediment containing the reduced contaminant.

A method for preparing the crude soil enzyme extract or isolated enzyme specific for reduction of specific environmental contaminants is disclosed wherein the reducing agent is extracted from soil by combining the soil with a solvent that solubilizes proteins. Preferably the extract is prepared from soil having a relatively high carbon content so that it contains a higher concentration of reducing agents. Further purification of the reducing agent can be achieved by protein precipitation and fractionation on chromatography columns. Semi-purified enzymes particularly useful for reducing specific classes of environmental contaminants and the processes for isolating these proteins are provided herein.

Contaminants that can b e reduced by the remediation method described herein include nitroorganics in general and specifically munitions such as TNT, RDX, HMX, nitrocellulose, and red water and pesticides such as methyl parathion and 2-(sec-butyl)-4,6-dinitrophenol, also known as Dinoseb; halogenated organic compounds such as halogenated organic solvents, halogenated pesticides and other industrial halogenated compounds such as and pentachlorophenol; cyano compounds such as benzonitrile, acetonitrile, and other industrial chemicals; anisoles such as anisole, dyes and pesticides containing methoxy moieties; and metals such as chromium.

BRIEF DESCRIPTION OF THE DRAWINGS

FIG. 1 is a graph of the relative reducing activity of a fractionated crude enzyme sediment extract. Fractionation was performed on a QAE Cellulose ion exchange chromatography column. The symbol ■ represents the concentration of protein as $\mu$g protein per 50 $\mu$l aliquot of each fraction. The symbol ● represents relative TNT-reducing activity. The symbol ▲ represents relative 4-chlorobenzonitrile-reducing activity.

FIG. 2 is a graph of relative reducing activity of the void volume fractions of FIG. 1 after fractionation on a SEPHAROSE™ CL-6B size exclusion chromatography column. The symbol ■ represents the concentration of protein as $\mu$g protein per 50 $\mu$l aliquot of each fraction. The symbol ● represents relative TNT-reducing activity. The symbol ▲ represents 4-chlorobenzonitrile-reducing activity. The open square symbol represents relative PCE-reducing activity.

FIG. 3 is a graph of relative reducing activity of fraction 18 of FIG. 2 after fractionation on a Phenyl SEPHAROSE™ hydrophobic interaction chromatography column. The symbol ■ represents the concentration of protein as $\mu$g protein per 50 $\mu$l aliquot of each fraction. The symbol ● represents relative TNT-reducing activity.

FIG. 4 is a graph of relative reducing activity of fraction 18 of FIG. 2 after fractionation on a Zn:Iminodiacetic Acid SEPHAROSE™ 6B chromatography column. The symbol ■ represents the concentration of protein as $\mu$g protein per 50 $\mu$l aliquot of each fraction. The symbol ● represents relative TNT-reducing activity. The symbol ▲ represents 4-chlorobenzonitrile-reducing activity.

FIG. 5 is a bar graph of percent TNT-reducing activity inhibition after addition of protease to fraction 18 of FIG. 2.

FIG. 6 is a graph of relative reducing activity for fractions 4, 13, and 19 from FIG. 2 after exposure to various temperatures. The symbol ● represents fraction 4. The symbol ▲ represents fraction 13. The symbol ■ represents fraction 19.

FIG. 7 shows chemical structures for the nitroorganics Disperse Blue 79, Disperse Red 5, parathion, dinoseb, RDX, HMX, and TNT.

FIG. 8 is a schematic representation of the stepwise reduction of substituted nitrobenzenes to the corresponding anilines in anaerobic sediments.

FIG. 9 is a graph of the reduction of nitrobenzene to nitrosobenzene, phenylhydroxyamine and aniline after incubation under anaerobic conditions with a sediment sample containing a nitrobenzene reducing agent. The black triangle symbol represents nitrobenzene, the black square symbol represents phenylhydroxyamine, the black circle symbol represents nitrosobenzene, the open square symbol represents aniline, and the asterisk symbol represents the sum of components.

FIG. 10 is a schematic representation of the stepwise oxidation of anilines to catechols, carbon dioxide and the corresponding acetates.

FIG. 11 is a graph showing the relationship between the disappearance rate constant of nitrobenzene and the organic carbon content of sediment when nitrobenzene is incubated under anaerobic conditions with various sediment samples containing a nitrobenzene reducing agent. ($R^2$=0.968; X1=0.442; C=-2.54)

FIG. 21 is a graph showing the Michaelis-Menton Kinetics for tetrabromoethene (PBE).

DETAILED DESCRIPTION OF THE INVENTION

Figure 12:
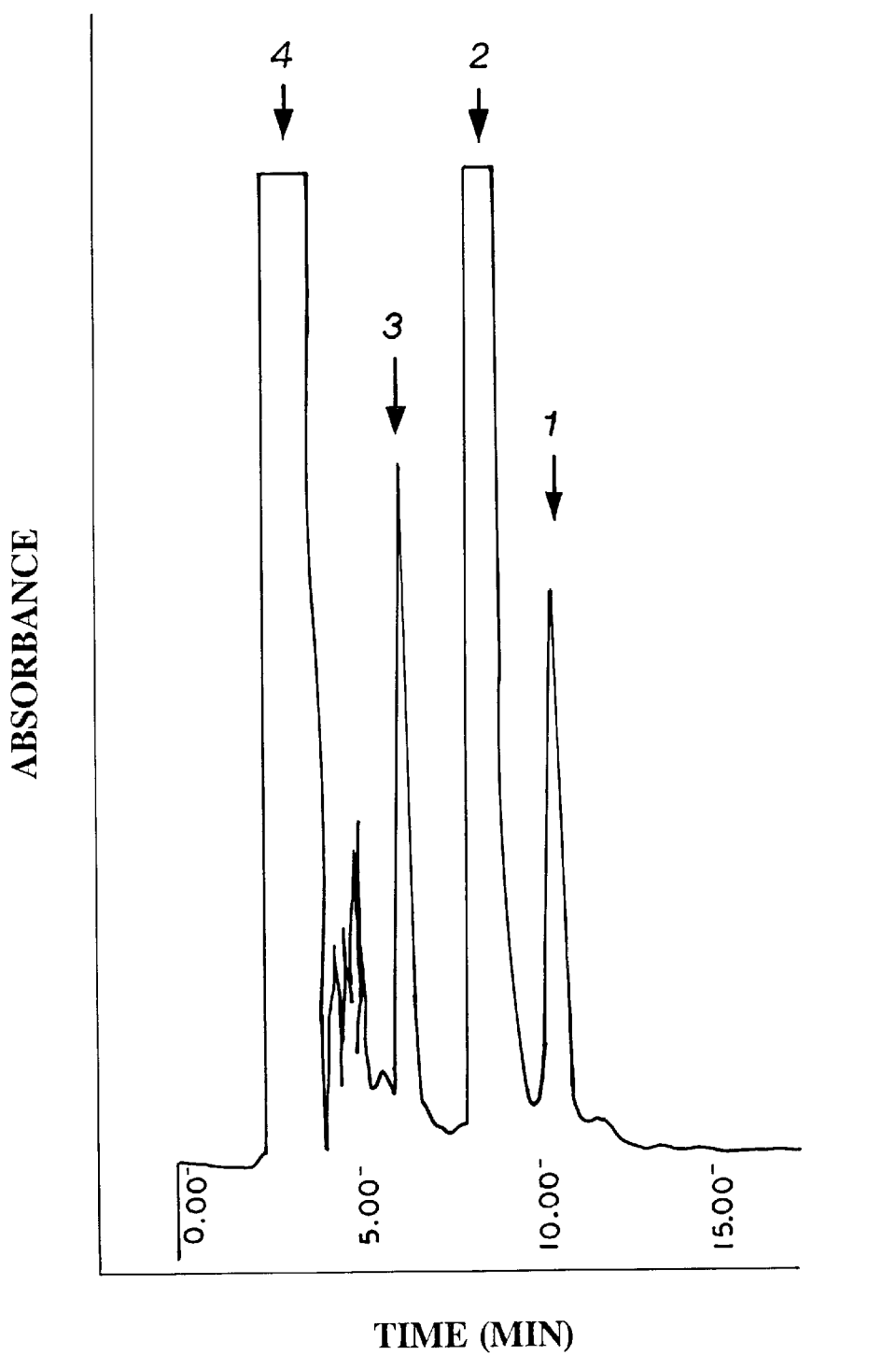
FIG. 12 is a representative HPLC chromatogram showing the relevant retention times and separation of TNT from the reduction products of TNT after incubation with a TNT reducing agent.

A method and composition for remediating a contaminant in soil, water, sediment, and aquifers to an environmentally safe product are provided. The environmental contaminant is first reduced by reacting the contaminant with a reducing agent. The reducing agent is an enzyme or combination of enzymes found in soil or sediment and is generally found in greater concentrations in soil having a higher organic content. The contaminant is reacted with the reducing agent by combining the contaminant with soil, a crude soil extract containing an amount of the reducing enzymes, or semi-purified or purified reducing enzymes specific for the reduction of a selected class of compounds sufficient to cause reduction. The reduced contaminant is then oxidized to an environmentally innocuous product by exposure to oxygen or air. The method is applicable to both in situ and batch processing and can be used to remediate contaminants such as nitroorganics, halogenated hydrocarbons, anisoles, cyano compounds, and metals as discussed in more detail below.

Reduction of Soil or Sediment Contaminants

In the method described herein, contaminated soil or sediment is first deprived of oxygen to create a substantially anoxic or anaerobic environment. While an anoxic environment is not essential for reduction of the contaminants by the reducing enzymes, it facilitates reduction by making the environment unfavorable to aerobic organisms. It has been discovered that aerobic organisms produce proteases that cleave and thereby inactivate the reducing enzymes used in the remediation method provided herein. In a preferred embodiment, the contaminated soil or sediment is deprived of oxygen by flooding the surface area of the soil or sediment with water. Contaminated sediment need not be flooded with water if it already exists in an anoxic state. The contaminated soil or sediment is then incubated for a sufficient period of time under the anoxic conditions to allow reduction of the contaminants by reducing agents either naturally present in the contaminated soil or sediment or by reducing agents added to the contaminated soil or sediment in the form of a crude enzyme extract or semi-purified enzyme extracted from soil. Mass transfer limitations can be overcome by mechanical mixing.

The term "reducing agents" as used herein refers to substances which facilitate the reduction of a compound. If the contaminated soil or sediment has a relatively low carbon content or if the degree of contamination is extensive and the soil therefore tails to contain an adequate concentration of reducing agents for rapid or complete reduction of the contaminants, a crude soil extract containing an adequate concentration of reducing enzymes for reduction of the contaminants, a semi-purified or purified enzyme or enzymes specific for reduction of the particular contaminant to be remediated, or a combination thereof may be added to the contaminated soil or sediment for more rapid and complete contaminant reduction. Soil or sediment having a "substantially high organic or carbon content" as used herein generally excludes soils containing predominantly sand or clay. For example, sediment collected from the Beaver Dam stream, near Athens, Ga., having a organic carbon content of 3% contains approximately 100 µg protein per liter of sediment. The amount of crude or purified enzyme added depends on the compound being remediated and the activity of the enzyme. For example, 1 µg of protein reduces $10^{-6}$ M TNT in approximately 15 minutes.

The extent of incubation depends on the carbon content of the soil or sediment which directly relates to the concentration of reducing enzymes in the soil and the amount of contamination as described above. In general, the higher the organic carbon content, the faster the contaminants are reduced. Preferably, the soil or sediment is incubated from one to four days. The addition of iron, preferably in the form of iron powder or filings provides an additional source of electrons, and, when added to the incubation mixture, greatly accelerates the reduction reaction.

Preferably, the soil or sediment being remediated is maintained in the pH range of 5 to 8 for both the oxidation and reduction steps. The heterogenous soil and water phase provides the pH buffering capacity. The Eh of the system is preferably −50 mV or less (relative to Ag/AgCl). In addition, the temperature of the contaminated area during remediation preferably ranges from 10 to 115° C. with the optimal temperature ranging between 25 and 37° C.

The sediment or flooded soil preferably contains a soil to water ratio ranging from 0.02:1 to 0.5:1 (g:g). It has been discovered that, in batch processes, the rate constants for reduction increase with increasingly greater soil to water ratios up to a ratio of 0.5:1.

Reduction of Water or Aquifer Material Contaminants

In the method described herein for remediation of contaminated water or aquifers, a sufficient amount of soil having a substantially high organic carbon content, a crude soil extract containing reducing enzymes, or a semi-purified or purified enzyme specific for reduction of the contaminant is combined with the contaminated water or aquifer material for reduction of the contaminants. As described above, the enzyme-containing soil and the water can be mixed by mechanical means to overcome mass transfer limitations. Contaminated water and aquifers are naturally anoxic and need no removal of oxygen during the incubation step.

The pH and Eh values, soil to water ratio, and extent of incubation are preferably the same as described above for the reduction of soil and sediment contaminants. As described above, the addition of iron to the incubation mixture, preferably in the form of iron powder or filings, greatly accelerates the reduction reaction.

Isolation of Reducing Agents a) Extraction

The crude enzyme extract and semi-purified or purified enzyme described above for reduction of soil, sediment, water, or aquifer material contaminants are extracted from a soil sample with one or more of a variety of different solvents. Preferably, the soil sample has a substantially high organic carbon content and therefore contains a concentrated amount of the reducing agent or agents as described above. Most preferably, the soil sample is a sediment rich in organic material such as the type of sediment found in a marsh or bog.

The source of the enzyme is believed to be a common aquatic plant, or weed, such as the hornwort moss. Therefore, the soil from which the enzyme is extracted should contain hornwort moss or should have previously supported the growth of the hornwort moss. The hornwort moss, also known as the horned liverwort, is a mosslike lower plant having no flowers. The hornwort moss is a creeping annual or perennial plant of the class Anthocerotopsida. In some classification systems, hornworts are grouped as horned liverworts in the subclass Anthocerotidae (class Hepaticae), class Anthocerotopsida, order Anthocerotales, or are classified in the division Anthocerotophyta. Hornworts usually grow on damp soils or on rocks in tropical and warm temperate regions. Rhizoids (rootlike structures) on the undersurface anchor the plant.

Optimal enzymatic yield is obtained when the soil sample is removed from beneath a water surface and is stored and transported under substantially anoxic conditions to limit proteolytic cleavage by aerobic organisms naturally present in the sample.

The crude enzyme extract is prepared from the soil sample by gently mixing approximately one volume of the sample with one or more volumes of solvent and then separating the solubilized proteins from the soil by mechanical methods known to those skilled in the art, such as centrifugation. Any solvent or mixture of solvents in which proteins are solubilized may be used to solubilize the reducing agent. A list of solvents useful for solubilizing the reducing reagent is set forth below in Table 1. Preferred solvents contain glycerol or methanol. The most preferred solvent is 20% glycerol in either water or a buffer, such as Tris or phosphate at pH 8. High quality solvents such as commercial high pressure liquid chromatography (HPLC) grade solvents are preferred to minimize additional contamination. HPLC grade solvents can be obtained from commercial chemical suppliers such as Burdick and Jackson, Musegon, Mich. The solvents sodium dodecyl sulfate (SDS), CTMA BR (cetyltrimethylammonium bromide), Triton X-100 and Tween 20 are detergents, whereas ammonium sulfate, urea, potassium phosphate and ammonium phosphate are salts.

TABLE 1

Solvents Useful for Extracting
Reducing Reagent 0.5% sodium dodecyl sulfate (SDS) in water
0.5% cetyltrimethylammonium bromide (CTMA Br) in water
0.5% Triton X-100 in water
0.5% Tween 20 in water
20% glycerol in water
20% glycerol + 0.5% SDS in water
20% glycerol + 0.5% CTMA Br in water
20% glycerol + 0.5% Triton X-100 in water
20% glycerol + 0.5% Tween 20 in water
500 mM KCl
500 mM KCl + 0.5% SDS in water
500 mM KCl + 0.5% CTMA Br in water
500 mM KCl + 0.5% Triton X-100 in water
500 mM KCl + 0.5% Tween 20 in water
2 M $NH_4SO_4$
2 M $NH_4SO_4$ + 0.5% SDS in water
2 M $NH_4SO_4$ + 0.5% CTMA Br in water
2 M $NH_4SO_4$ + 0.5% Triton X-100 in water
2 M $NH_4SO_4$ + 0.5% Tween 20 in water
6 M urea
6 M urea + 0.5% SDS in water
6 M urea + 0.5% CTMA Br in water
6 M urea + 0.5% Triton X-100 in water
6 M urea + 0.5% Tween 20 in water
$K_2HPO_4$ + $KH_2PO_4$ pH 7 (0.5 M)
$K_2HPO_4$ + $KH_2PO_4$ pH 7 (0.5 M) + 0.5% SDS in water
$K_2HPO_4$ + $KH_2PO_4$ pH 7 (0.5 M) + 0.5% CTMA Br in water
$K_2HPO_4$ + $KH_2PO_4$ pH 7 (0.5 M) + 0.5% Triton X-100 in water TABLE 1-continued Solvents Useful for Extracting
Reducing Reagent $K_2HPO_4 + KH_2PO_4$ pH 7 (0.5 M) + 0.5% Tween 20 in water
0.5 M $NH_4HPO_4$
0.5 M $NH_4HPO_4$ + 0.5% SDS in water
0.5 M $NH_4HPO_4$ + 0.5% CTMA Br in water
0.5 M $NH_4HPO_4$ + 0.5% Triton X-100 in water
0.5 M $NH_4HPO_4$ + 0.5% Tween 20 in water
20% glycerol + 50 mm Tris-HCl, pH 8.0 in water Most preferably, the sample and solvent mixture is allowed to stand for several minutes until the majority of the particular matter of the sample has precipitated and the proteins have been solubilized. The supernatant is decanted and centrifuged for approximately 20 minutes at 5000 rpm to remove the finer particulate matter. The extraction and centrifugation steps can be repeated to increase yield. The resulting supernatant is a crude enzyme extract that can be used to reduce environmental contaminants without further purification if desired.

b) Protein Precipitation

The crude enzyme extract can be concentrated and further purified by precipitating the proteins from the extract. Salt precipitation with a concentration sufficient to achieve 80–90% saturation with a salt such as ammonium sulfate is preferred.

c) Desalting

A semi-purified enzyme extract can be prepared by resuspending the precipitate in water and simultaneously removing the salt and fractionating the proteins on a desalting or size exclusion column such as a SEPHADEX™ G-25sf column, available from Pharmacia, Inc., Piscataway, N.J. The SEPHADEX™ G-25sf column fractionates molecules having a molecular weight greater than 5000, therefore the fraction eluting in the void volume of the G-25 column contains molecules having a molecular weight greater than 5000. This semi-purified high molecular weight enzyme fraction contains most of the reducing activity for all classes of contaminants remediated by the method described herein except metals. Therefore, the enzymes useful for remediation of nitroorganics, halogenated hydrocarbons, anisoles, and cyano compound contaminants all have a molecular weight greater than 5000. Metal contaminants, such as $K_2CrO_4$, are reduced by the low molecular weight fraction from the G-25 column (less than 5000 daltons) or the total extract. Therefore, the enzyme or compounds specific for reduction of metal contaminants have a molecular weight less than 5000 daltons.

d) Additional Purification

The enzyme extract can be further purified using conventional protein purification techniques known to those skilled in the art, alone or in combination, for the isolation of substantially pure enzyme. Protein purification techniques include separation of the active enzyme by charge fractionation using an ion exchange column such as an QAE anion exchange or DEAE SEPHAROSE™ anion exchange column (Pharmacia, Piscataway, N.J.); by size fractionation using a size exclusion column such as a CL-6B SEPHAROSE™ column (Pharmacia); by hydrophobicity fractionation using a phenyl column such as a phenyl SEPHAROSE™ CL-4B column (Pharmacia); and by amino acid metal binding properties using a zinc affinity column such as a Zinc Iminodiacetic Acid-SEPHAROSE™ 6B Fast Flow Column (Sigma Chemical Co., St. Louis, Mo.).

Enzymes specific for the reduction of nitroorganics, halogenated hydrocarbons, anisoles, cyano compounds and metals can be isolated from the crude enzyme extract using a combination of the above-mentioned protein fractionation techniques as described in more detail below. Fractions are assayed for activity as described below, and active fractions are pooled prior to fractionation by a subsequent separation mechanism.

e) Assay for Reducing Activity

Fractions collected during each step of the enzyme purification method described herein can be assayed for reducing activity by combining an aliquot of each fraction with a solution containing a compound from the class of contaminants to be remediated. The mixture is incubated and assayed for the presence of reduced contaminants by analytical methods known to those skilled in the art, such as HPLC and GC.

Protein concentrations for each fraction can be determined using commercially available reagents such as the BIORAD™ Protein Reagent (BioRad, Richmond, Calif.) in accordance with the manufacturer's instructions or by conventional protein analysis methods well known to those skilled in the art.

f) Isolation of Reducing Agent with Monoclonal Antibodies

The reducing agent, or a particular enzyme specific for the reduction of a particular class of contaminants such as a nitroreductase, nitrilase, demethylase, or dehalogenase can be isolated from a soil sample, or a soil sample can be tested for the presence of such an enzyme, with the aid of a detectable polyclonal or monoclonal antibody in accordance with methods well known to those skilled in the art. The production of monoclonal antibodies specific for a particular enzyme or protein is also achieved by methods well known to those skilled in the art, such as the methods described in *Antibodies, A Laboratory Manual*, Ed Harlow, Cold Spring Harbor Laboratory, Cold Spring Harbor, N.Y. 1988.

Basically, monoclonal antibodies are produced from a hybridoma cell generated by fusing a normal antibody-producing lymphocyte from the spleen of an experimental animal, such as a mouse or rat, recently immunized with the protein of interest, to a myeloma cell line that does not synthesize its own immunoglobulin and is deficient in the enzyme hypoxanthine-guanine phophoribosyltransferase (HGPRT), which catalyzes reactions of the bases hypoxanthine and guanine with 5-phophoribosyl-1-pyrophosphate to form the nucleotides inosine-5'-P(IMP) and guanosine-5'-P (GMP), respectively. The hybrid cells are selected over either parental cell by culturing in a medium containing hypoxanthine, aminopterin, and thymidine (HAT medium). The myeloma cells, lacking HGPRT, cannot survive because the de novo synthesis of GMP is blocked by the folate antagonist aminopterin, and the normal lymphocytes grow very slowly in HAT medium, whereas the hybrid cells, in which a functional HGPRT gene is supplied by the lymphocyte genome, grow rapidly and form large colonies that are readily distinguishable from those of the slowly growing lymphocytes. Clones of hybrid cells producing the desired antibody are identified by a suitable assay procedure and grown into larger cultures. The homogenous immunoglobulin produced by such a cloned hybrid is a monoclonal antibody having specificity for the enzyme.

The monoclonal antibody can be made detectable by attachment of a detectable label. The various types of labels and methods of labelling monoclonal antibodies are well known to those skilled in the art. Several specific labels are set forth below.

For example, the label can be a radiolabel such as, but not restricted to, $^{32}P$, $^3H$, $^{14}C$, $^{35}S$, $^{125}I$, or $^{131}I$. Detection of a radiolabel can be by methods such as scintillation counting, gamma ray spectrometry or autoradiography.

The label can also be a Mass or Nuclear Magnetic Resonance (NMR) label such as, for example, $^{13}C$, $^{15}N$, or $^{19}O$. Detection of such a label can be by Mass Spectrometry or NMR.

Fluorogens can also be used to label the monoclonal antibodies. Examples of fluorogens include fluorescein and derivatives, phycoerythrin, allo-phycocyanin, phycocyanin, rhodamine, Texas Red or other proprietary fluorogens. The fluorogens are generally attached by chemical modification. The fluorogens can be detected by a fluorescence detector.

The monoclonal antibodies can alternatively be labelled with a chromogen to provide an enzyme or affinity label. For example, the antibody can be biotinylated so that it can be utilized in a biotin-avidin reaction which may also be coupled to a label such as an enzyme or fluorogen. The probe can be labelled with peroxidase, alkaline phosphatase or other enzymes giving a chromogenic or fluorogenic reaction upon addition of substrate. For example, additives such as 5-amino-2,3-dihydro-1,4-phthalazinedione (also known as LUMINOL™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used.

A label can also be made by detecting any bound antibody complex by various means including immunofluorescence or immuno-enzymatic reactions. Such labels can be detected using enzyme-linked immunoassays (ELISA) or by detecting a color change with the aid of a spectrophotometer.

Reducing Agent Characteristics

The active reducing agent consists of one or more enzymes believed to be derived from the hornwart moss. The enzyme is soluble in water and may be a membrane-bound enzyme complex or portion thereof, possibly a glycoprotein. It is believed that the enzyme is an electron carrier that transfers electrons to the contaminants in the presence of an electron source (anoxic conditions) and removes electrons from the contaminants in the presence of an electron sink (oxic conditions).

The reducing agent extracted from soil or sediment as described herein is abiotic in that neither microbial activity nor metabolism is required. Furthermore, with the exception of the dehalogenase enzyme described in more detail below, which is oxygen sensitive, the reducing agent does not require strict anaerobic conditions for activity. Treatment of the reducing agent with protease K, a digestive enzyme that hydrolyses peptide bonds in polypeptide chains, decreases the ability of the reducing agent to reduce contaminants thereby demonstrating that the active component of the reducing agent is a protein.

Isolation and Characterization of the Nitroorganic Reducing Agent

An enzyme specific for reduction of nitroorganic compounds was isolated from the semi-purified enzyme extract described above by the following procedure.

Charge

Void volume fractions from the SEPHADEX™ G-25sf column containing proteins having a molecular weight greater than 5000 daltons were collected and pooled. The pooled fractions were concentrated with a ZETAPREP™ 15 disk (Pharmacia, Piscataway, N.J.), adjusted to pH 8.6 with a 100 mM Tris buffer, and subjected to low pressure ion exchange fractionation by passage through a QAE or DEAE SEPHAROSE™ anion exchange column. The mobile phase was 100 mM Tris buffer, pH 8.6. Under these conditions, fractions having a neutral or positive charge at pH 8.6 passed through the column into the void volume while fractions having a negative charge were retained on the column. Fractions were collected and assayed for protein concentration and the ability to reduce the nitroorganic compounds TNT and 4-chlorobenzonitrile as described above. The highest levels of activity for reducing both TNT and 4-chlorobenzonitrile were found in the fractions having a neutral or positive charge at pH 8.6 (void volume fractions) as shown in FIG. 1.

Size

The fractions having high reducing activity were pooled, precipitated to reduce the volume, resuspended in 50 mm Tris, at pH 7, and subjected to fractionation by size exclusion chromatography by passage through a SEPHAROSE™ CL-6B column. The mobile phase was 50 mm Tris, pH 7. Fractions were once again assayed for protein content and the ability to reduce the nitroorganic compounds TNT and 4-chlorobenzonitrile. The molecular weight range for each fraction was determined by comparing the elution time of the active fractions to the elution time of proteins standards having known molecular weights. Fractions containing molecules having a molecular weight between 300,000 and 400,000 daltons, between 49,000 and 80,000 daltons, and between 18,500 and 27,000 daltons exhibited the highest levels of TNT reducing activity as shown in FIG. 2, while fractions containing molecules having a molecular weight of approximately 600,000 daltons exhibited the highest levels of 4-chlorobenzonitrile reducing activity and molecules having a molecular weight of approximately 400,000 to 600,000 daltons had the highest levels of 1,2,3,4-tetrachloroethene (PCE) reducing activity.

Hydrophobicity

The fractions having the largest molecular weight molecules with TNT-reducing activity were pooled, precipitated, reconstituted in 1.7 M ammonium sulfate, pH 7 and passed through a Phenyl SEPHAROSE™ CL4B column for separation and fractionation on the basis of hydrophobicity. Molecules were eluted with a linear gradient of 1.7 M ammonium sulfate to 1.7 M ammonium phosphate, pH 7. The gradient was begun after five fractions were collected. Under these conditions, hydrophilic components pass through the column quickly while hydrophobic components are retained and are eluted as the concentration of ammonium sulfate in the mobile phase is reduced. Fractions were assayed for protein content and the ability to reduce TNT. The highest TNT reducing activity was observed in the hydrophobic fractions, with maximal reducing activity contained in fraction 32, as shown in FIG. 3.

Metal-binding Ability

The active fractions were pooled, precipitated, reconstituted in 1 M potassium chloride and passed through a Zn Iminodiacetic acid-SEPHAROSE™ CL-6B Fast Flow column. In this column, any material that does not bind zinc is eluted early. The sample was loaded onto the column in 1 M potassium chloride in 50 mM $K_2PO_4$, washed with five void volumes of 50 mM potassium phosphate buffer, pH 7, containing 1 M KCl and eluted with a linear gradient from 1 M potassium chloride to 2 M ammonium sulfate in phosphate buffer, pH 7. As shown in FIG. 4, fractions containing TNT-reducing activity are found in fractions 16–18 and bind zinc to some extent, whereas fractions containing 4-chlorobenzonitrile-reducing activity are found in fractions 6–8 and bind zinc to a lesser extent. A metals analysis of the active fractions revealed that the TNT-reducing enzyme contains iron whereas the 4-chlorobenzonitrile reducing enzyme does not contain any metals.

Enzymatic Digestion

Treatment of an aliquot from pooled fractions 16–18 from FIG. 4, having TNT-reducing or fractions 6–8, having 4-chlorobenzonitrile-reducing activity, with increasingly larger concentrations of pronase E, protease K or subtilisin caused inhibition of TNT-reducing activity, as shown in FIG. 5. Treatment with the proteases chymotrypsin and trypsin, known to cleave proteins only at aromatic amino acids, caused no inhibition of TNT reducing activity. Therefore, the TNT reducing enzyme has few available aromatic amino acids. The activity of the nitrilase was inhibited by both trypsin and chymotrypsin.

Temperature Effects

FIG. 6 shows the effect of elevated temperature on low, intermediate, and high molecular weight fractions eluted from the SEPHAROSE™ agarose CL-6B size exclusion column. (The molecular weights of these fractions are shown in FIG. 2.) Elevation of temperature had little effect on the high molecular weight fraction (fraction 4), moderate effect on the intermediate molecular weight fraction (fraction 13) and a greater effect on the low molecular weight fraction (fraction 19).

Kinetics

The kinetics of the purified TNT-reducing agent and the purified nitrile-reducing agent, isolated as pooled fractions 16–18 from the Zn-Iminodiacetic acid-SEPHAROSE™ agarose CL-6B column, respectively, are set forth below in Table 2.

TABLE 2

Reducing Agents Kinetics

| Compound | (Concentration) | Half-life |
|---|---|---|
| TNT | (1.5 × 10-6) | 15 minutes |
| TNT | (3.0 × 10-6) | 30 minutes |
| TNT | (7.5 × 10-6) | >5 hours |
| nitrobenzene | (1.0 × 10-6) | 28 hours |

Molecular Weight

The size of the TNT-reducing enzyme, as determined by polyacrylamide gel electrophoresis, is approximately 316,000 daltons and is believed to contain six subunits having a molecular weight of approximately 19,000, two subunits having a molecular weight of approximately 37,000, two subunits having a molecular weight of approximately 66,000, and at least two iron molecules. The TNT-reducing enzyme exhibits a dumbbell shape when viewed by scanning tunnelling microscopy.

The size of the 4-chlorobenzonitrile-reducing enzyme has a molecular weight of approximately 600,000 and is believed to be composed of four subunits each having a molecular weight of approximately 150,000.

Isolation and Characterization of the Halogenated Hydrocarbon Reducing Agent

An enzyme specific for reduction of halogenated hydrocarbons, or a dehalogenase, was isolated from the semi-purified enzyme extract described above by the procedure described above for the isolation of the nitroorganic reducing agent with the exception that all the buffers were kept anaerobic.

Sequential dehalogenation of a halogenated hydrocarbon with the dehalogenase results in the formation of the dehalogenated hydrocarbon. The final product appears to be carbon dioxide, a compound that is acceptable to the environment.

Charge

As described above, void volume fractions from the SEPHADEX™ G-25sf column containing proteins having a molecular weight greater than 5000 daltons were collected, pooled, concentrated and subjected to low pressure ion exchange fractionation by passage through a QAE or DEAE Sepharose™ anion exchange column so that fractions having a neutral or positive charge at pH 8.6 passed through the column into the void volume while fractions having a negative charge were retained on the column. Fractions were collected and assayed for protein concentration and the ability to reduce the halogenated hydrocarbon tetrabromoethene (TBE) as described above. The highest levels of activity for reducing TBE were found in the fractions having a neutral or positive charge at pH 8.6 (void volume fractions) as shown in FIG. 1.

Size

The fractions having high reducing activity were pooled, fractionated by size exclusion chromatography by passage through a Sepharose™ CL-6B column as described above, and once again assayed for protein content and the ability to reduce the halogenated hydrocarbon TBE. The molecular weight range for each fraction was determined as describe above. Fractions containing molecules having a molecular weight of approximately 293,000 daltons exhibited the highest levels of TBE reducing activity.

Metal-binding Ability

A metals analysis of the active fractions revealed that the dehalogenase enzyme contains copper and iron.

Temperature and pH

Figure 18:
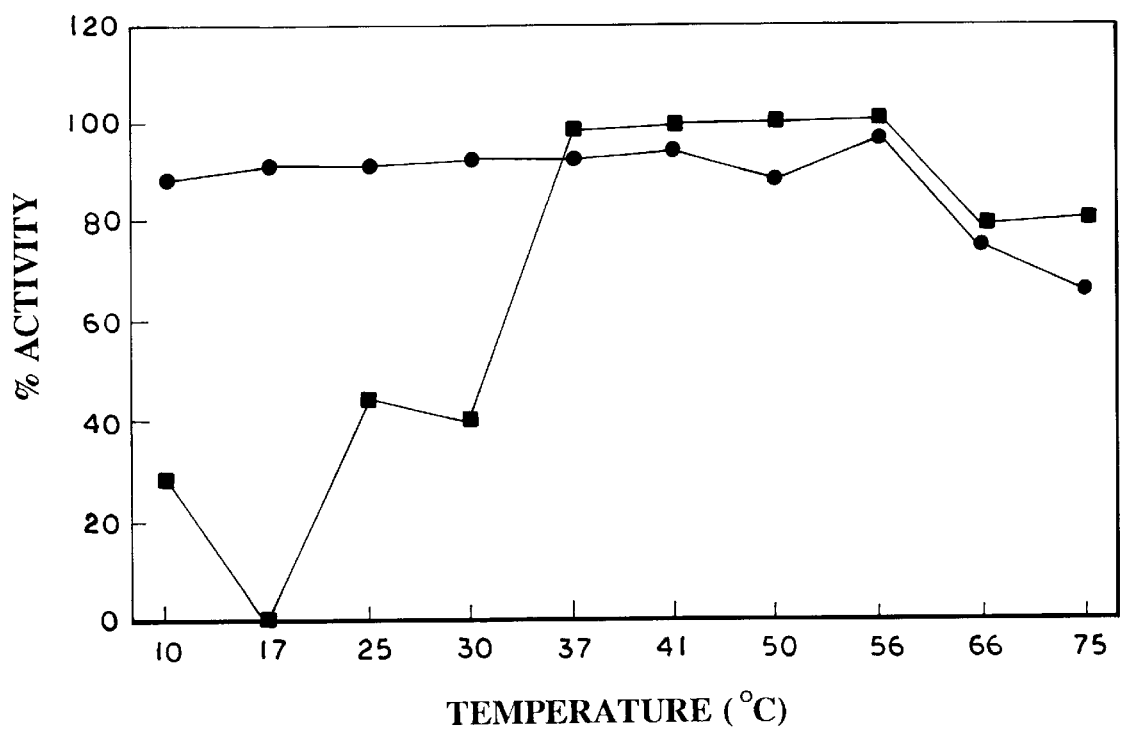
FIG. 18 is a graph showing reactivity (percent activity) of tetrabromoethene (PBE) and hexachloroethane (HCA) with protein as a function of temperature. The black circle symbol represents HCA. The black square symbol represents PBE.
Figure 19:
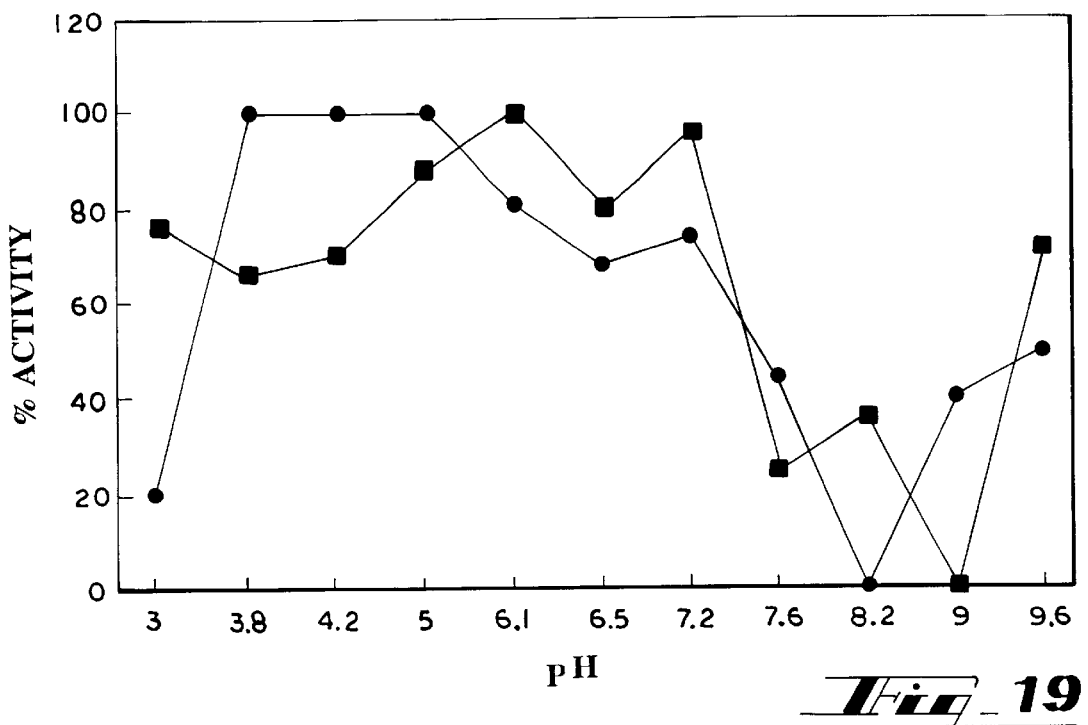
FIG. 19 is a graph showing reactivity (percent activity) of tetrabromoethene (PBE) and hexachloroethane (HCA) with protein as a function of pH. The black circle symbol represents HCA. The black square symbol represents PBE.

The purified dehalogenase exhibited maximal activity at a temperature between approximately 10 and 50° C. and at a pH between approximately 3 and 7. The maximal activity for HCA dehalogenation was observed at a temperature between approximately 10 and 50° C., as shown in FIG. 18, and at a pH between approximately 3.8 and 6.0, as shown in FIG. 19, whereas the maximal activity for PBE dehalogenation was observed at a temperature between approximately 25 and 50° C., as shown in FIG. 18, and at a pH between approximately 5.0 and 7.0, as shown in FIG. 19.

Kinetics

The kinetics for the reduction of the following halogenated alkanes and alkenes: tetrabromoethene (PBE), hexachloroethane (HCA), tetrachloroethene (PCE) and trichloroethene (TCE), by the purified dehalogenase, using microgram quantities of protein in and near saturated solutions of the halogenated hydrocarbons, are set forth below in Table 3.

TABLE 3

Dehalogenase Reducing Agents Kinetics

| Compound | (Concentration) | Half-life |
|---|---|---|
| PBE | (30 μM) | 1100 minutes |
| HCA | (30 μM) | 200 minutes |
| PCE | (60 μM) | 200 minutes |
| PCE | (100 μM) | 600 minutes |
| TCE | (60 μM) | 200 minutes |

Figure 17:
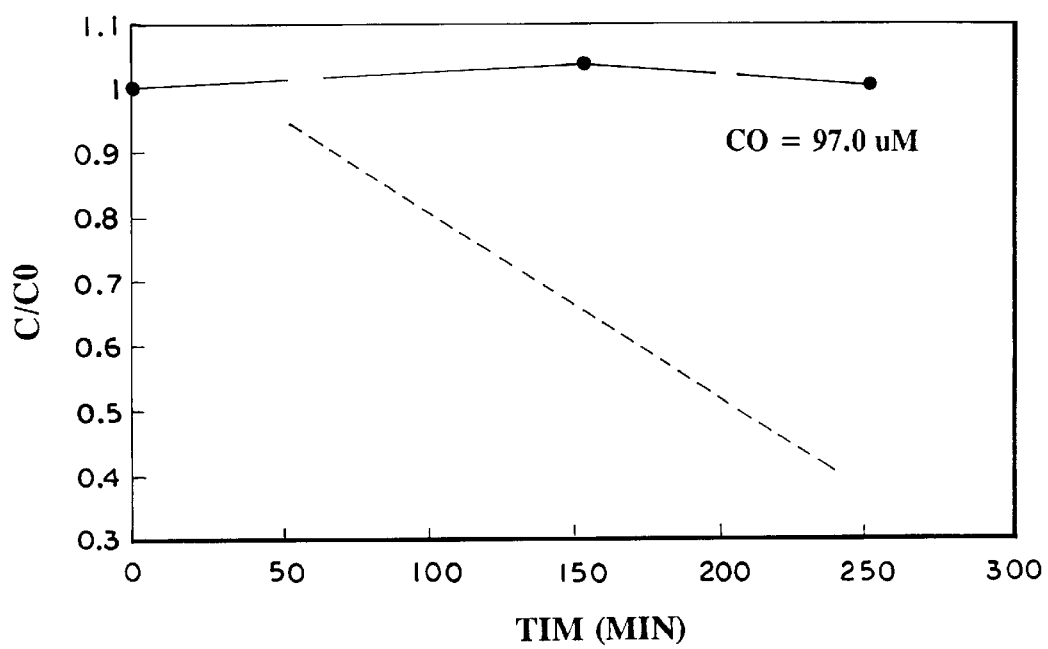
FIG. 17 is a graph showing the enzymatic reaction of trichloroethane (TCE) as concentration divided by initial concentration versus time. The initial concentration was 97.0 $\mu$M. The black circle symbol represents the control. The dash symbol represents TCE.
Figure 20:
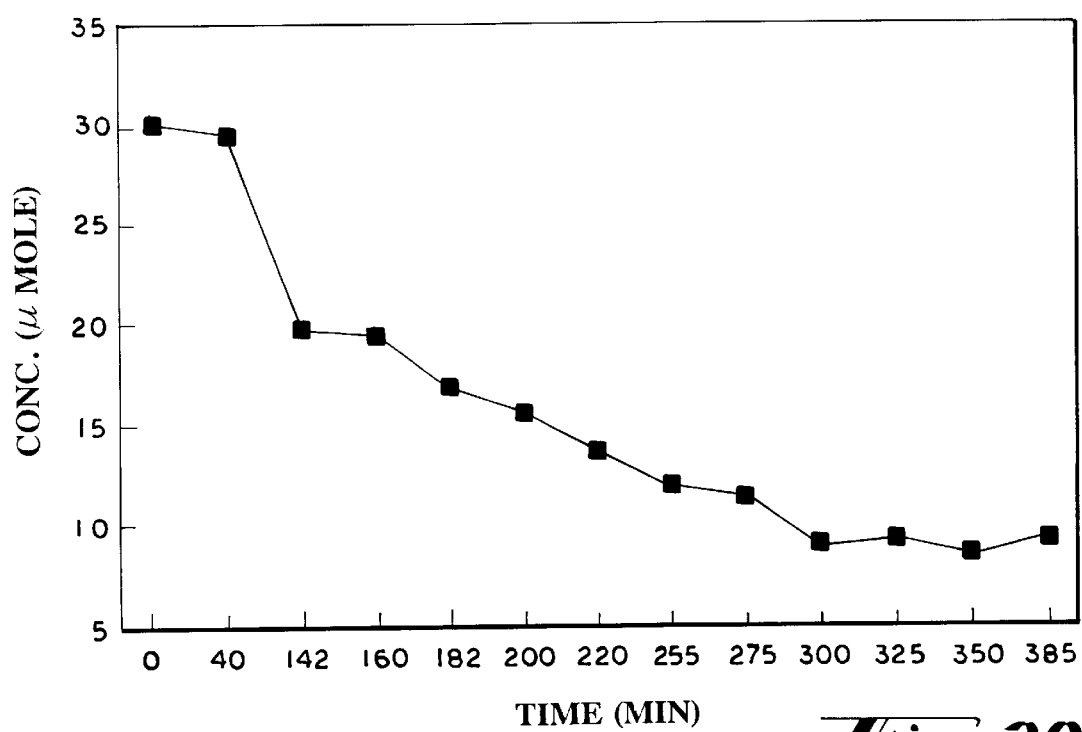
FIG. 20 is a graph showing a decrease in the concentration of hexachloroethane (HCA) after reaction with the dehalogenase enzyme.

A graph showing a reduction in the concentration of TCE by the dehalogenase over time is shown in FIG. 17. A graph showing reduction of HCA by the dehalogenase over time is shown in FIG. 20. The Michaelis-Menton kinetics for reduction of PBE are shown in FIG. 21.

It was observed that ascorbic acid functions as a co-factor for the dehalogenase. In addition, competition experiments revealed that the dehalogenase preferentially reduces alkenes over alkanes.

Molecular Weight

The size of the dehalogenase, as determined by polyacrylamide gel electrophoresis, is approximately 293,000 daltons and is believed to contain two subunits having a molecular weight of approximately 90,000 daltons, two subunits having a molecular weight of approximately 39,000 daltons, two subunits having a molecular weight of approximately 28,000 daltons, and one or more copper and iron molecules.

Oxidation of Reduced Contaminants

Contaminants that have been reduced by the reducing agent as described above are oxidized to environmentally safe compounds by the addition of oxygen. Oxygen is preferably added by bubbling air into the incubation mixture. Exposure of the reduced contaminants to oxygen can also be achieved, for contaminated soil or sediment that has been flooded with water, by simply removing the water by evaporation or other methods known to those skilled in the art.

The remediation method can be carried out in a variety of reactors including batch reactors. Alternatively, the contaminated soil can be remediated in situ without removing the soil from the ground.

Classes of Compounds Reduced

The remediation method can be used to degrade a wide variety of environmental contaminants including, but not limited to, nitroorganic compounds, halogenated organic compounds, cyano compounds, anisoles, and metals. It will be understood by those skilled in the art that the remediation method may be used to degrade other contaminants that are similarly reduced and oxidized.

a) Nitroorganic Compounds

The remediation method provided herein is particularly useful in reducing nitroorganic compounds contaminating soil, sediment, water or aquifer materials. Nitroorganic compounds are defined herein as nitroaromatics and nitroaliphatics and specifically include munitions such as trinitrotoluene (TNT), hexahydro-1,3,5-trinitro-1,3,5-triazine (RDX), octahydro-1,3,5,7-tetranitro-1,3,5,7-tetraazocine (HMX), N-methyl-N-2,4,6-tetra-nitroaniline (Tetryl), nitrocellulose, and munition processing wastewater such as the TNT manufacturing by-product known as "red water". The described remediation method is also useful for remediation of nitroorganic pesticide contaminants such as methyl parathion and 2-(sec-butyl)-4,6-dinitrophenol, also known as Dinoseb. In addition, the remediation method is useful for remediating nitrobenzenes, benzonitriles such as 4-chlorobenzonitrile, Disperse Blue 79, Disperse Red 5, and azo compounds such as azobenzene.

The term "azo compound" as used herein refers to a compound containing a –N═N— moiety. Disperse Blue 79, Disperse Red 5, and azo-compounds, are industrial chemicals.

The chemical structures for Disperse Blue 79, Disperse Red 5, parathion, dinoseb, RDX, HMX, and TNT are shown in FIG. 7.

FIG. 8 shows chemical formulas for reduction of several nitroaromatic compounds by reducing agents in soil to the corresponding anilines in an anaerobic environment. Oxidation of anilines produces catechols which are degraded to carbon dioxide and the corresponding acetates, as shown in FIG. 10.

b) Other Compounds

The method provided herein is useful for remediation of halogenated hydrocarbons contaminating soil, sediment, water or aquifer materials. Halogenated hydrocarbons are defined herein as halogenated organic compounds or solvents such as hexachloroethane (HCA), tetrachloroethene (PCE), tetrabromoethene (PBE), trichloroethene (TCE) and trichloroethylene, halogenated pesticides and other industrial chemicals such as halogenated aromatics and pentachlorophenol (PCP).

The method provided herein is useful for remediating soil, sediment, water or aquifer materials contaminated by cyano compounds such as benzonitrile, acetonitrile, and other industrial chemicals; anisoles such as anisole, dyes and pesticides containing methoxy moieties; and metals such as chromium and arsenic, especially $K_2CrO_4$.

The remediation method will be further understood with reference to the following non-limiting examples.

EXAMPLE 1

In Vitro Reduction of para-substituted nitrobenzenes by Six Anaerobic Sediments

A series of para-substituted nitrobenzenes were shown to undergo abiotic reduction to the corresponding anilines in several anaerobic sediment samples.

Materials

Nitrobenzene, 4-nitrotoluene, 4-nitroanisole, 4-chloronitrobenzene, 4-bromonitrobenzene, 4-nitrobenzonitrile, 1,4-dinitrobenzene, 4-toluidine, 4-anisidine, 4-chloroaniline, 4-bromoaniline, 4-aminoacetophenone, 4-aminobenzonitrile, 4-nitroaniline, catechol, nitrosobenzene (all at least 97% pure; Aldrich Chemical Co., Inc., Milwaukee, Wis.), 4-nitroacetophenone (97% pure; Pfaltz and Bauer, Inc., Waterbury, Conn.), aniline (99.5% pure; Fluka Chemical Corp., Hauppauge, N.Y.) were used without further purification. Phenylhydroxylamine, m.p. 80–82° C., was synthesized by reducing nitrobenzene with zinc in accordance with the method of Kamm, O., *Org. Syn.* 4:57–58 (1924) and recrystallized from hexane. The identity and purity of these compounds was confirmed by HPLC. and gas spectrometry-mass spectrometry (GC-MS) using a Finnigan MAT (Finnigan, San Jose, Calif.) automated gas chromatograph/EI mass spectrometer. Acetonitrile (Burdick and Jackson, Musegon, Mich.), sodium hydroxide (Fisher Scientific Co., Pittsburgh, Pa.), nitric acid and hydrochloric acid (J. T. Baker Chemical Co., Phillipsburg, N.J.) were of high purity.

Sediment

Anaerobic sediments were collected from several different sites. Three of these sediments were collected near Athens, Georgia from a slow moving river (the Oconee River), a slow moving high sediment load stream (Beaver Dam), and a small pond (Bar H pond). A fourth sediment was collected from a bog near Gaston, Ill. (Morgan's Muck). A fifth sediment was collected from an uncontaminated aquifer near Quincy, Florida (Florida Aquifer). The sixth sample was collected from a peat bog near Bilthoven, The Netherlands (Loosdrechtsche Plassen). The sediments and associated water, except the Florida aquifer sample, were collected by scooping up the first 5 to 10 cm of bottom sediment into 1 liter canning jars at a depth of 30 to 50 cm below the water surface. The jars were capped before being brought to the surface. The samples were sieved through a 1 mm sieve in the laboratory to remove debris and stored in a glove box in a nitrogen atmosphere until used. The aquifer sample was collected using a hollow stem auger with a split spoon sampler in a fresh drilled well 15 to 20 meters deep. The sediment was covered with groundwater, transported to the laboratory and stored in a glove box under a nitrogen atmosphere until used.

Sediment Eh readings were taken in the glove box with a Markson 1202 combination platinum electrode that was placed in the sediment. (Markson, Houston, Tex.) The electrode was calibrated against a standard ferrous-ferric poised standard (Light et al., 1972). If the electrode did not read to within ±10 mV of Eh=750 mV, the electrode was cleaned with 10% HCl (v/v) followed by 10% $H_2O_2$ (v/v). The measurement was taken when the Eh reading stabilized (approximately 20 min). The fraction organic carbon, $F_{oc}$, (w/w) was measured using air dried sediment by coulometric titration using an automated instrument (Dohrman, Santa Clara, Calif.) in accordance with the method of Lee, C. M. and D. L. Macalady, Inter. *J. Environ. Anal. Chem.* 35:2219–225 (1988).

Sediment pH was measured in the glove box with a portable Corning pH/TempMeter 4 equipped with a Ross combination electrode (Orion Research, Inc., Boston, Mass.). After calibrating the pH meter with pH 4.00, 7.00, and 10.00 buffers (Fisher Scientific Co., Pittsburgh, Pa.), the pH was measured by inserting the electrode into a stirred sediment slurry. Stirring was stopped and the pH was recorded when the reading stabilized (approximately 10 min).

Liquid Chromatography

A Waters 501 chromatographic pump equipped with a Kratos 757 variable wavelength UV-visible detector (Kratos Analytical Instruments, Ramsey, N.J.) and a Rheodyne 7125 injector using a 20 μl sample loop (Rheodyne, Inc., Cotati, Calif.) was used for reverse phase HPLC. Typically, the column was a pH stable Hamilton PRP-1 column, 250 mm long×4.1 mm i.d., 10 μm particle size (Hamilton Co., Reno, Nev.). The analytical column was protected with a cartridge guard column containing a PRP-1 cartridge, 10 mm×4.6 mm i.d., 10 μm particle size (Alltech Associates, Inc., State College, Pa). Typically the mobile phase was acetonitrile-:water (60:40, v/v) at pH 12 (adjusted with 10 N NaOH), and the flow rate was 1.0 ml/min at 1500 psi. These conditions were used for the analysis of both disappearance of the parent compound and product formation. The mobile phase for catechol analyses was acetonitrile:water (20:80, v/v) at pH 1.75 (adjusted with concentrated $HNO_3$).

Detector wavelength varied with the compound of interest: nitrobenzene, 262 nm; 4-nitrotoluene, 272 nm; 4-nitroanisole, 310 nm; 4-chloronitrobenzene, 278 nm; 4-bromonitrobenzene, 278 nm; 4-nitroacetophenone, 262 nm; 4-nitrobenzonitrile, 272 nm; 1,4-dinitrobenzene, 262 nm; aniline, 233 nm; 4-toluidine, 235 nm; 4-anisidine, 232 nm; 4-chloroaniline, 240 nm; 4-bromoaniline, 240 nm; 4-aminoacetophenone, 230 nm; 4-aminobenzonitrile, 275 nm; 4-nitroaniline, 220 nm; catechol, 262 nm; nitrosobenzene, 320 nm; phenylhydroxylamine, 262 nm. Product formation was confirmed by GC/MS and quantitated by HPLC through comparison with known standards. The GC/MS system used for product formation was a Hewlett-Packard 5890 GC with a 15 m HP-1 0.2 mm capillary column with 0.33 μm film thickness connected to a Hewlett-Packard 5970 mass selective detector (Hewlett Packard Co., Palo Alto, Calif.).

Distribution Coefficient

The soil to water ratio was measured by weighing triplicate aliquots of sediment-water slurry, then evaporating at 110° C. overnight and determining the dry weight. The distribution coefficient ($K_d$) of the compounds were determined in conjunction with most kinetic experiments. This was accomplished by centrifuging spiked sediment-water samples after vortexing 1 min and removing a 3.0 ml aliquot of the aqueous phase. The aqueous phase was extracted with 1.0 ml acetonitrile. The remaining sediment phase was extracted with 1.0 ml acetonitrile and centrifuged. Both extracts were analyzed via HPLC. Corrections were made for the water remaining in the sediment phase.

Kinetic Procedures

Kinetic experiments were conducted by a batch method in which 5 ml of a stirred sediment-water slurry was pipetted into a series of 10 ml screw-capped test tubes. The tubes were spiked with 50 μm of a $1.0 \times 10^{-3}$ M solution of the desired nitrobenzene derivative in acetonitrile or methanol. The test tubes were capped with screw caps fitted with teflon or n-butyl rubber lined septa, removed from the glove box and vortexed for 10 seconds. All sediment sample manipulations except for the initial sieving were conducted within the glove box. The test tubes were incubated at the desired temperature (±1° C.) in a water or oil bath with gentle shaking. Kinetic studies conducted above 100° C. were carried out in sealed glass ampoules. Periodically a test tube was sacrificed for analysis by adding 1.0 ml acetonitrile then vortexing 1 min. The tube was centrifuged (15 minutes at 4000 rpm) and the supernatant analyzed by HPLC. Typical sample recoveries were in excess of 95% (w/w). To examine the role of pH, the pH of sediments was altered by the dropwise addition of either 10 N NaOH or concentrated HCl to within 0.5 pH units of the desired value and allowed to equilibrate 24 hours. The pH was measured and adjusted again as necessary. The samples were not used until the desired pH had stabilized for 24 hours.

Results

The eight para-substituted nitrobenzene compounds were reduced by the general stepwise reduction mechanisms shown in FIG. 8. Nitrobenzene gave aniline as the stable product with phenylhydroxylamine and nitrosobenzene as reactive intermediates.

As shown in Table 4, the para-substituted nitrobenzene compounds were reduced when the pH of the sediments was between 5.3 and 10.55. However, at pH 3.85 and 2.50, no reduction of the para-substituted nitrobenzene compounds could be detected within experimental error. Additionally, sediment flocculation and agglutinization of the solids was observed at this low pH. At pH 7, $K_d$ was 3.4 and Eh was 105 mV. The organic carbon fraction was 0.0166.

The disappearance rate constant for nitrobenzene correlated best with the organic carbon content of the solid phase as shown in FIG. 11.

TABLE 4

Disappearance rate constants for nitrobenene reduction in Beaver Dam sediment over pH range 2.5–10.6

| pH | Sediment/$H_2O$ ratio | $k_{obs}(10^{-4}m^{-1})^a$ | $k_{corr}(10^{-4}m^{-1})^b$ |
|---|---|---|---|
| 2.5 | 0.0288 | no observed rxn | 0.25 + 0.025 |
| 3.85 | 0.0281 | no observed rxn | 0.12 + 0.012 |
| 5.3 | 0.0433 | 4.0 ± 0.21 | 4.6 ± 0.24 |
| 7.0 | 0.0305 | 3.8 ± 0.18 | 4.2 ± 0.20 |
| 7.75 | 0.0314 | 7.7 ± 0.70 | 8.5 + 0.77 |
| 9.15 | 0.0244 | 8.6 ± 0.57 | 9.3 ± 0.62 |
| 10.55 | 0.0520 | 6.6 ± 1.0 | 7.8 + 1.2 |

[a]Observed first-order disappearance rate constant and standard deviation.
[b]Calculated maximum rate assuming a 10% analytical method error.

EXAMPLE 2

In Vitro Reduction of Nitrobenzene Compounds by Four Anaerobic Sediments

Nitrobenzene, 4-ethylnitrobenzene, 4-(n-butyl) nitrobenzene and 4-(n-octyl)nitrobenzene in anaerobic sediment samples were reduced to the corresponding anilines.

Chemicals and Sediments

Nitrobenzene (99+%), 4-ethylnitrobenzene (99+%), 4-ethylaniline (99+%), 4-(n-butyl)aniline (97%), and 4-(n-octyl)aniline (99%) from Aldrich Chemical Co., Milwaukee, Wis., and reagent grade aniline from the J. T. Baker Chemical Co., Phillipsburg, N.J., were used without further purification. Formaldehyde (37%) solution, with 12% Methanol, from J. T. Baker Chemical Co.), hydrogen peroxide (30% solution from J. T. Baker Chemical Co.), mercuric chloride (Fisher Scientific Co., Pittsburgh, Pa.), and isopropanol (spectrograde, Burdick and Jackson, Musegon, Mich.) were used as chemical sterilants. Sodium azide (Fisher Scientific Co.), toluene (Spectrograde, Burdick and Jackson), and m-cresol (99+%) (Aldrich Chemical Co. Inc., Milwaukee, Wis.) were used as metabolic inhibitors. All solvents used were of high purity grade from Burdick and Jackson.

4-(n-Butyl)nitrobenzene and 4-(n-octyl)nitrobenzene were synthesized by slowly adding a 3.0 M methylene chloride solution (2.5 ml) of the corresponding aniline to a stirred 0.7 M methylene chloride solution (45 ml) of 3-chloroperoxybenzoic acid (tech., 80–85%, from Aldrich Chemical Co. Inc.). After refluxing for one hour and cooling, the mixture was washed with 1.0 N NaOH, then 0.1 N HCl, then water, and then the organic layer was dried over sodium sulfate. The methylene chloride was evaporated under a nitrogen stream, leaving a yellow-orange liquid. NMR and IR spectra showed no remaining amino compound, and both nitro compounds gave a single peak via liquid chromatography. Yields for 4-(n-butyl)- and 4-(n-octyl)nitrobenzenes were 77 and 62%, respectively.

Thioglycollate indicator was used to check anaerobic sterility. The thioglycollate indicator agar was made by bringing thioglycollate medium (14.5 g, Difco Laboratories, Detroit, Mich.), BACTO-AGAR™ (5 g, Difco Laboratories), and 0.1% resazurin indicator (5 ml, resazurin from Sigma Chemical Co., St. Louis, Mo.) to a boil in 500 ml of water, with subsequent cooling. The resazurin indicator turns the nutrient medium red if conditions become aerobic. Tryptone Glucose Extract Agar (Difco Laboratories) was used to assay for aerobic sterility.

Sediments

Anaerobic sediment samples from four bodies of water near Athens, Ga. were used. Three of these (known as Hickory Hill, Memorial Park, and Bar-H) were samples from lakes; the fourth (Beaver Dam) was from a stagnant, slow moving stream. Sediments were collected by scooping up samples in 1 quart canning jars at a depth of 1–2 feet below the water surface. The jars were capped, brought back to the laboratory, passed thorough a 1 mm sieve, and stored in a glove box under a nitrogen atmosphere until used. Sediments were used within two weeks of collection.

Liquid Chromatography

A Tracor 950 chromatographic pump equipped with a Tracor 970A variable wavelength detector (Tracor Instruments, Austin, Tex.) and a Rheodyne 7120 injector with a 50 $\mu$l sample loop (Rheodyne, Inc., Cotati, Calif.) was used for liquid chromatography. The column was a Micromeritics Microsil™ C-18, 25 cm length×4.6 mm I.D., 5 $\mu$m particle size (Micromeritics Instrument Co., Norcross, Ga.). A guard column (2 mm I.D.×7 cm length) was filled first with a small amount of Microsil™ 5 $\mu$m packing and then with Whatman 30–38 $\mu$m pellicular C-18 guard column packing (Whatman SA, France). For 4-(n-octyl) nitrobenzene, the solvent was 70:15:15 acetonitrile:tetrahydrofuran:water. The elution time was 4.3 minutes behind the solvent front (flow rate 1.5 ml/min). For all other compounds, the solvent was 70:30 acetonitrile:water. Nitrobenzene, 4-ethylnitrobenzene, and 4-(n-butyl) nitrobenzene eluted 2.3, 3.0 and 5.5 minutes behind the solvent front, respectively. In each case, the corresponding aniline eluted slightly earlier than its nitro analog. The wavelength used was 280 nm.

Kinetic Experiments

The pH was determined before each experiment using an Orion 91.62 probe (Orion Research, Inc, Boston, Mass.) by gently agitating the probe in the solid phase at the bottom of the jar. In all four sediment samples, the pH was maintained between 6.8 and 7.1. Sediment Eh readings were also taken before each experiment by placing a Markson 1202 combination platinum electrode (Markson, Houston, Tex.) in the sediment jar overnight to equilibrate before taking readings. The Eh generally read between −170 and −230 mv.

Aliquots (5 ml) of the desired sediment, drawn while stirring the sediment with a glass rod in the glove box, were transferred to a series of 15 ml screw cap test tubes. The tubes were capped with Hungate (open top) screw caps (fitted with teflon lined septa) and brought outside of the glove box. The tubes were spiked with 5 $\mu$l of a tetrahydrofuran standard ($10^{-2}$ M) of the desired nitroaromatic compound. The tubes were briefly vortexed. At selected time intervals, one tube from the series was sacrificed by quenching with acetonitrile (2 ml) and vortexing for 30 seconds. The remaining sample tubes were inverted four times at this point. For nitrobenzene, 4-ethylnitrobenzene, and 4-(n-butyl)nitrobenzene, the tubes were then centrifuged (tabletop centrifuge, 2500 rpm for 20 minutes) and the supernatant (5 ml) was filtered through a 925 mm Millipore™ filter (Millipore Corp., Bedford, Mass.). The sample was then ready for analysis. For 4-(n-octyl)nitrobenzene, hexane (4 ml) was added to the quenched sample, and it was vortexed again for 1 minute. An aliquot (3 ml) of the hexane layer was removed, evaporated under a nitrogen stream, and redissolved into acetonitrile (5 ml). The sample was then ready for analysis.

For runs with added chemical sterilant or inhibitor, the appropriate amount of chemical was added to the sediment 16 hours before spiking with nitrobenzene. For kinetic runs without the sand and silt fractions, the sediment was allowed to settle for 1.5 hours under nitrogen after stirring before aliquots were drawn. For kinetic runs with sediment associated water only, sediment was centrifuged as above, and the resulting supernatant was used for kinetic runs. Recoveries of the nitroaromatic compounds 4 hours after spiking from twice-autoclaved sediment (220° C., 20 psi×20 m) were 84±3% for nitrobenzene, 4-ethylnitrobenzene, and 4-(n-butyl)nitrobenzene, and 100±5% for 4-(n-octyl) nitrobenzene.

Sediment/Water Ratios

Triplicate aliquots (5 ml) of sediment were transferred to tared test tubes. After reweighing, the samples were centrifuged as above, the supernatant removed, and the pellet dried in an oven overnight at 95° C. After cooling, the dried samples were weighed again. Ratios were calculated by dividing the dry weight of the sediment by the weight of the aqueous phase.

Distribution Coefficients

Distribution coefficients ($K_d$) for the four nitroaromatics were determined at 3 minutes, 1 hour, 3 hours, and 4 hours after spiking in twice autoclaved sediment (as above). Samples were periodically inverted. For nitrobenzene and 4-ethylnitrobenzene, the spiked sample was centrifuged (as above) after the desired incubation time, and supernatant (3.5 ml) was removed and filtered as described above. To the remaining supernatant and pellet, acetonitrile (2 ml) was added, and the sample was vortexed for 30 seconds. The sample was then centrifuged again, and the supernatant (2–2.5 ml) was filtered. After correcting for the supernatant contribution to the pellet extract, the $K_d$ (6.25 µg compound/g dry solid)/(µg compound/g supernatant) was calculated using the sediment/water ratios calculated for the experiment. Recoveries were quantitative for both compounds. For 4-(n-octyl)nitrobenzene, sediment diluted 10-fold with supernatant from another sample jar (obtained by centrifugation) was used. After the desired incubation time, the sample was centrifuged, and 4 ml of supernatant was removed and centrifuged again. A portion of this second supernatant (3 ml) was removed and extracted with hexane (2 ml). An aliquot of the hexane layer (1.5 ml) was then evaporated under a nitrogen stream, and the residue redissolved in acetonitrile (1 ml) before analysis. To the pellet and remaining supernatant, acetonitrile (2 ml) and hexane (4 ml) were successively added, vortexing for 30 seconds and 1 minute afterwards, respectively. An aliquot of the hexane layer (3 ml) was then evaporated and the residue was redissolved in acetonitrile (5 ml) for analysis. The $K_d$S were calculated after correcting for the sample handling steps. The recovery was 86±4% for 4-(n-octyl)nitrobenzene.

Diluted sediment was also used to determine the $K_d$ for (n-butyl)nitrobenzene. The $K_d$ was determined in a similar manner as for 4-(n-octyl)nitrobenzene, except that acetonitrile alone (4 ml) was sufficient to extract the pellet, and after a second centrifugation, an aliquot of the extract (3 ml) was filtered and analyzed directly. Recoveries were only 60±6% for 4-(n-butyl)nitrobenzene, but this method was found to give the best recoveries of the extraction methods attempted. $K_d$ were found to remain nearly constant with time for all of the above compounds.

Aerobic and Anaerobic Sterility Tests

Aerobic sterility was determined by applying 0.1 ml of treated sediment to sterilized, hydrated tryptone glucose extract agar spread on a Petri dish and watching for growth within 5 days. Anaerobic sterility was determined by stabbing treated sediment into 5 ml plugs of sterilized thioglycollate indicator agar under nitrogen in 15 ml test tubes. Sterility was indicated by the retention of the pink oxygenated band at the top of the plug, the absence of gas formation, and no visible growth in the anaerobic portion of the agar over a five day period.

Polarography

The reduction potential of the four nitroaromatics was measured in aqueous solution (10 mM) at pH 6.8 (0.1 M phosphate) using square wave polarography. The instrument was an EG & F Princeton Applied Research Corp. Digital Polarograph 82 (EG & F Instruments, Ltd., United Kingdom) used in the HMDE mode, with a medium drop size. The purge time was 4 minutes (helium). The scan range was −100 to −600 mV (relative to Ag/AgCl); pulse size, −20 mV; step size, −5 mV; drop settle delay, 400 ms; sweep delay, 0 m; preintegration time, 2000 µs; integration time 12,562 s; and current gain 256.

Results

As shown in Table 5, nitrobenzene was readily degraded in all samples of nitroaromatic anaerobic sediment gathered from the four different water bodies. The half-lives for the reduction of nitrobenzenes in anaerobic sediment samples are on the order of a few hours as shown in Table 6. A graph showing the reduction of nitrobenzene to aniline over a two hour period of time is shown in FIG. 9.

Nitrobenzene in sediment which had been autoclaved exhibited a reduced rate of reduction to aniline. Chemical sterilization with formaldehyde had no effect on the rate of reduction to aniline. Therefore, the reducing component is heat labile but not labile to formaldehyde when bound to sediment.

TABLE 5

Reduction of nitrobenzene in four anaerobic sediments

| Sediment | % OM[a] | Eh(mv) | p | $K_d$ | t½(min) | $r^2$ |
|---|---|---|---|---|---|---|
| Beaver Dam | 5.6 ± 0.3 | −170 | 0.112 ± 0.016 | 3.9 ± 0.8 | 142 ± 51 | 0.980 |
| Bar-H | 2.2 ± 1.0 | −170 | 0.060 ± 0.006 | 2.6 ± 0.5 | 21 | 0.999 |
| Hickory Hill | 1.8 ± 1.0 | −230 | 0.052 ± 0.002 | 2.6 ± 0.4 | 142 | 0.999 |
| Memorial Park | 4.3 ± 0.2 | −250 | 0.038 ± 0.003 | 9.0 ± 1.0 | 120 | 0.991 |

[a]Deterinined by heating dry sediment at 425° C. for 20 hours, corrected for water of adhesion (obtained by heating dry sediment at 70° C. for 3 days)

TABLE 6

Pseudo-first-order disappearance rate constants for reduction of nitrobenzene and three 4-substituted nitrobenzenes

| Compound | t½(min) |
|---|---|
| nitrobenzene | 53 |
| 4-ethylnitrobenzene | 74 |
| 4-(n-butyl) nitrobenzene | 120 |
| 4-(n-octyl) nitrobenzene | 1140 |

EXAMPLE 3

Kinetics of Reduction of 15 Halogenated Hydrocarbons in Four Anoxic Sediment Samples Sediment-water slurries were collected from the ponds known as Vechten Pond, Bilthoven; Breukelveen, and Loosdrechtse Plassen and the slow-moving stream known as Dommel, all in The Netherlands. Samples were collected by scooping the first 5–10 cm of bottom sediment into glass jars. The jars were completely filled with sediment and water and capped under the water surface. Sediment samples were stored at 20° C. until used for experiments. Prior to use, the samples were sieved through a 1 mm wire sieve to remove debris. The sediment to water ratio (g/g) of samples was determined by placing 10 ml aliquots of the thoroughly mixed sediment-water sample in weighed, open 50 ml jars. Consequently the water was evaporated during one day at 80° C. and the jars were reweighed. Each determination was repeated five times.

Kinetics experiments were performed using a batch method in which sediment aliquots were distributed into a series of test tubes and spiked with a known concentration of a halogenated hydrocarbon under a nitrogen atmosphere. All halogenated hydrocarbons were purchased from Aldrich Chemical Co., Milwaukee, Wis. A tube was sacrificed for analysis of the concentration of chemical in the sample at specific time intervals during incubation. For each experiment, 10 ml aliquots of sediment were placed in 20 ml test tubes. A stock solution of each halogenated compound was made in methanol (Burdick and Jackson, Musegon, Mich.) such that a 10 $\mu$l addition of chemical into 10 ml sediment gave the desired initial experimental concentration. Sample tubes were spiked with 10 $\mu$l halogenated hydrocarbon. After vortexing, the tubes were incubated at 22° C. and were periodically mixed. At specific time intervals, 2 ml of acetonitrile (Burdick and Jackson) was added to the tubes to quench the reaction. Tubes were vortexed for 1 minute, the sediments extracted with 4 ml cyclohexane (Burdick and Jackson) and vortexed again for 2 minutes. The cyclohexane layer was recovered from the tubes after centrifugation at 3500–4000 rpm for fifteen minutes, placed in a clean tube and stored at −30° C.

Cyclohexane extracts were analyzed using a Carlo Erba (Milan, Italy) 4160 gas chromatograph equipped with an electron-capture detector and a Hewlett Packard (Avondale, Pa.) 3392 integrator. The column used was a fused silica open tubular column with CP-sil-5CB as the stationary phase (25 m×0.32 mm). The relative concentrations of the compounds were calculated by comparing peak areas of samples at given times against the peak area of the zero time sample.

A Metrohm (Herisau, Switzerland) pH meter was used for both the pH and Eh measurements. Eh values were measured using a platinum Ag:AgCl reference electrode. All Eh values are reported versus SHE. All pH and Eh measurements were performed under a nitrogen atmosphere.

GC-MS analyses were performed using a Hewlett Packard model 5890A gas chromatograph interfaced with a Finnigan (San Jose, Calif.) 4500 quadrupole mass spectrometer. The column was a fused silica capillary column with CP Sil-5 as the stationary phase.

The NMR spectra were recorded at 200 MHz on a Bruker (Karlsruhe, Germany) AC 200 NMR spectrometer interfaced with an ASPECT 3000 computer. The spectra were recorded using $CDCl_3$ (deuterated chloroform) as the solvent with TMS (tetra-methyl silane) as the internal standard.

The results of the kinetics studies for 15 halogenated hydrocarbons are shown in Table 7. The Eh and pH did not change appreciably during the experiment. Below an Eh value of −50 mV, the disappearance rate constant was essentially independent of the Eh. The rate of disappearance of all the compounds that reacted was first-order through at least two half-lives. The halogenated hydrocarbons exhibited a wide range of reactivity with the shortest half-life of about ten minutes for tetraiodoethene to no detectable reaction after 90 days of incubation for perflurodecaline, perfluorohexane and DDT. A calculated maximum rate constant and minimum half-life can be arrived at by assuming a 10% experimental error in the analysis of the compound after 90 days reaction time. All of the halogenated hydrocarbons were stable to hydrolysis under the redox reactions employed in this example.

TABLE 7

Kinetic data and reaction parameters for reduction of halogenated hydrocarbons in sediment samples under anaerobic conditions

| Compound | Initial Conc. (mol/l) | Rate Constant k (min-1) | Half life (hour) |
|---|---|---|---|
| Tetraiodoethene[1] | 9.60E-06 | 9.22E-02 | 0.1 |
| Hexachloroethane[2] | 7.32E-08 | 2.47E-02 | 0.5 |
| Hexachloroethane[3] | 7.32E-08 | 7.62E-03 | 1.5 |
| 1,2-Dibromo-1,2-dichloroethane[1a] | 1.21E-06 | 5.44E-03 | 2.1 |
| 1,2-Dibromo-1,2-dichloroethane[1a] | 1.21E-06 | 4.54E-03 | 2.5 |
| Hexachloroethane[1] | 7.32E-08 | 2.33E-03 | 5.0 |
| Hexachloroethane[4] | 7.32E-08 | 1.22E-03 | 9.5 |
| Carbontetrachloride[2] | 1.6E-06 | 1.16E-03 | 10.0 |
| 2,3-Dibromobutane[1a] | 1.19E-06 | 1.10E-03 | 10.5 |
| 2,3-Dibromobutane[1a] | 1.19E-07 | 9.15E-04 | 12.6 |
| 1,2-Dibromoethane[1] | 9.28E-07 | 7.13E-04 | 16.2 |
| Hexachlorocyclohexane[1] | 5.70E-07 | 1.51E-04 | 76.5 |
| Tetrachloroethene[1] | 9.79E-08 | 4.05E-05 | 285.5 |
| Iodobenzene[1] | 2.2E-06 | 2.55E-05 | 453.0 |
| Hexachlorocyclohexane[1] | 5.09E-07 | 2.36E-05 | 489.4 |
| DDT[1] | 1.44E-06 | NR | — |
| Perfluorodecaline[1] | 1.44E-06 | NR | — |
| Perfluorohexane[2] | 2.01E-06 | NR | — |

[1]Sediment obtained from Vechten Pond: pH 7.2, Eh-139 mV, Organic Carbon 6.0%.
[2]Sediment obtained from Breukelveen: pH 7.6, Eh-145 mV, Organic Carbon 29%.
[3]Sediment obtained from Dommel: pH 7.5, Eh-155 mV, Organic Carbon 0.53%
[4]Sediment obtained from Loosdrechtse Plassen: pH 7.7, Eh-128 mV, Organic Carbon 32.6%
NR = no reactivity observed durinmg incubation; * = Diastereomer

EXAMPLE 4

In vitro Remediation of Hexachloroethane in 18 Sediment or Aquifer Samples

The sorption-corrected rate constants for the reduction of the halogenated hydrocarbon hexachloroethane (Aldrich Chemical Co., Milwaukee, Wis.) by reducing agents present in 18 different sediment, soil and aquifer samples were correlated with organic carbon content.

Rate constants for reduction of hexachloroethane were determined generally as described in Example 3.

Organic carbon content was determined by the method of Lee and Macalady, *Inter. J. Environ. Anal. Chem.* 35:219–225 (1988).

Correlation of Rate Constants with Organic Carbon Content

Disappearance rate constants for the reduction of hexachloroethane by reducing agents in 18 different sediment, soil and aquifer samples are listed in Table 8, in the order of decreasing rate constants ($k_{obs}$). The data in Table 8 suggest a relationship between the rate constants and organic carbon content of the samples.

TABLE 8

Measured ($k_{obs}$) and sorption corrected ($k_{corr}$) disappearance rate constants for hexachloroethane in selected sediments and aquifer samples.

| SEDIMENT SOURCE | Fraction OC | Sediment conc. (g.g$^{-1}$) | log $K_{obs}$* min$^{-1}$ | log $k_{corr}$# min$^{-1}$ |
|---|---|---|---|---|
| BarH | 0.022 | 0.08 | −1.301 | −1.081 |
| BarH | 0.022 | 0.09 | −1.455 | −0.248 |
| HickoryH | 0.018 | 0.11 | −1.585 | −0.519 |
| Breukelveen | 0.29 | 0.045 | −1.607 | 0.407 |
| BeaverD | 0.056 | 0.2 | −1.699 | −0.570 |
| MemorP | 0.043 | 0.055 | −1.721 | −0.841 |
| BarH | 0.022 | 0.075 | −1.721 | −0.586 |
| Loosdr. Plassen | 0.33 | 0.050 | −2.118 | −0.018 |
| Vechten Pond | 0.06 | 0.087 | −2.632 | −1.019 |
| EPA-B1 | 0.009 | 0.1 | −2.745 | −1.847 |
| Dommel | 0.0053 | 0.469 | −2.915 | −1.613 |
| EPA-13 | 0.03 | 0.1 | −3.089 | −1.708 |
| EPA-11 | 0.015 | 0.1 | −3.104 | −2.007 |
| EPA-6 | 0.0072 | 0.1 | −3.350 | −2.535 |
| Lula, aq | 0.000065 | 0.161 | −4.267 | −4.233 |
| Blythville, aq | 0.00012 | 0.142 | −4.359 | −4.306 |
| Blythville, aq | 0.00012 | 0.613 | −4.361 | −4.167 |
| Lula, aq | 0.000065 | 0.689 | −4.521 | −4.393 |

*observed rate constants
sorption corrected rate constants: $k_{corr} = k_{obs} * (1 + \rho * k_d)$
aq = aquifer Sorption Corrected Rate Constants The sorption corrected rate constant ($k_{corr}$) in which $k_{obs}$ is corrected for the fraction of the compound sorbed is given by the following equation, in which P denotes the sediment concentration (g. g$^{-1}$):

$$k_{corr} = k_{obs}*(1+P*K_d) \qquad (4)$$

The $k_{corr}$ values are included in Table 8 and were calculated using a log $K_{ow}$ (octanol-water partition coefficient) value of 4.61. Linear regression analyses showed that this correction for sorption increases the correlation between organic carbon content and the disappearance rate constant.

Although there are other factors that contribute to the reduction of hexachlorethane, organic carbon content accounts for about 91% of the variance of the data.

EXAMPLE 5

Nitroreduction of 2,4,6-Trinitrotoluene (TNT) with Crude Enzyme Extract

The effects of initial TNT concentration on the reaction order in anaerobic sediment samples, the reaction of TNT with crude proteins extracted from high organic carbon content sediments, and the effect of iron powder on TNT degradation in flooded soil were analyzed.

To monitor the disappearance of TNT and formation of its products in anaerobic sediment samples, TNT and its reduced products were extracted from water/sediment samples with acetonitrile (Burdick and Jackson, Musegon, Mich.) and analyzed by HPLC equipped with a UV detector as follows. The solvent was 30% water (pH 10) and 70% acetonitrile at a flow rate of 0.7 ml/min. Absorbance was detected at a wavelength of 238 nm. A representative HPLC chromatogram for TNT and its reduced products is shown in FIG. 12. The dinitro and monoamino toluene isomers (Peak 2) eluted at same retention time, however, these isomers can be separated and identified by GC/MS. The two diamino, mononitrotoluene isomers (Peak 3) also co-eluted. Triaminotoluene (Peak 4) eluted with the solvent front. TNT (Peak 1) and standards for identification of its reduced products were obtained from the U.S. Army Research, Development, and Engineering Center, Picatinny Arsenal, N.J.

The dependence of initial concentration of TNT on reaction order was investigated. The initial concentrations of TNT used were 0.25 ppm, 2.5 ppm and 125 ppm. The saturated concentration of TNT is about 125 ppm in water.

Figure 13:
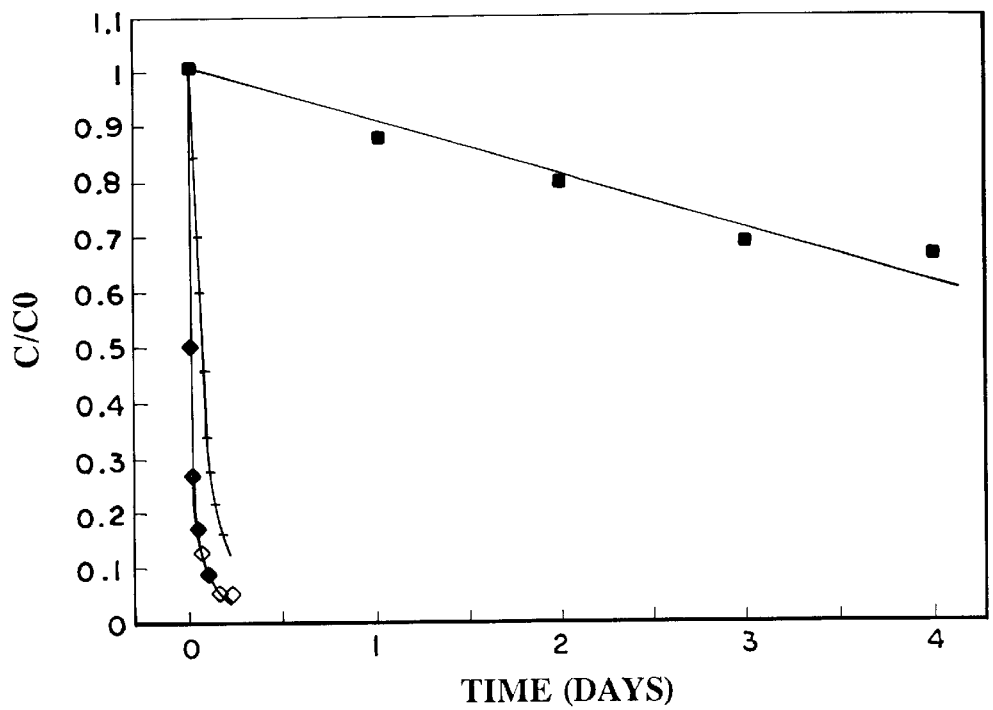
FIG. 13 is a graph showing the rate of reduction of various concentrations of TNT in an anaerobic sediment sample. The symbol ■ represents an initial TNT concentration of 125 ppm. The symbol + represents an initial TNT concentration of 2.5 ppm. The open diamond symbol represents an initial TNT concentration of 0.25 ppm. (p=0.12±0.01; pH=6.5; Eh=-368 mv (Ag/AgCl))

Sediments were collected from a stagnant, slow moving stream near Athens, Ga. These sediments were passed through a 1 mm sieve. Aliquots of 5 ml of sediment slurries were transferred to a series of 15-ml screw cap test tubes and kept under anaerobic condition. The sediment/water ratio was 0.12, pH was 6.5 and Eh value was −368 mv (vs. Ag/AgCl). A certain amount of concentrated TNT solutions were spiked into sediment samples to achieve three concentrations of TNT. At given time intervals, one tube of sample from the series was extracted by adding 1 ml of acetonitrile, vortex-mixing for 1 min and centrifuging. The supernatant was transfer centrifuged again and analyzed. FIG. 13 shows percentage of TNT remaining in the water/sediment sample as a function of time for three different concentrations of TNT. The rate of change of TNT concentration is a constant when the concentration of TNT is 125 ppm or greater. Beyond this concentration, the reaction proceeds at a rate independent of both concentrations of TNT and sediment. Therefore, at high TNT concentration, the reaction rate is zero order. When the concentration of TNT was decreased to 2.5 ppm, the concentration of TNT decreased exponentially with time. Plotting ln(c/c0) against time by using least-square regression method, a straight line was obtained with the value of $r^2$ equal to 0.99. This reaction of TNT is a first order reaction and half-life is 90 min. With 0.25 ppm TNT, the reduction rate was fast. After a certain elapsed time, the concentration change slowed down. A plot of 1/c as a function of time and regression analysis showed that the TNT reduction in water/sediment system appeared to follow a second order reaction. This result assumed that both TNT and sediment activity have the same initial stoichiometric concentration. Consequently, the results indicated that the reaction order of TNT in the water/sediment system depends on TNT initial concentration.

The reducing activity of a protein extract isolated from a high organic carbon sediment was analyzed after introduction into either an aqueous solution or a low organic carbon content system such as aquifer material. One ppm TNT solution was mixed with 0.5 g/ml aquifer sample as the control. One ppm TNT solution was mixed with 15 μg/ml of the TNT-reducing protein extract isolated from fraction 18 of FIG. 2 as described above and incubated for 24 hours. The purpose of incubation was to let the substrate, TNT, associate with the denatured subunits to recover the original active form of the enzyme. This procedure was followed by the "Microbial Metabolism of Aromatic Nitriles" study described by David B. Harper, Biochem. J. 167:685–692 (1977). After the incubation period, the incubated sample was spiked with concentrated TNT solution so that the final TNT concentration was 1 ppm.

To determine whether the protein extract would bind to aquifer material and retain activity in water, 15 μg/ml of protein extract was incubated with 0.5 g/ml aquifer sample for 24 hours before the TNT solution was added. The aquifer material had been collected from Columbus Air Force Base in Georgia. The organic carbon content in this aquifer was 0.027%.

Figure 14:
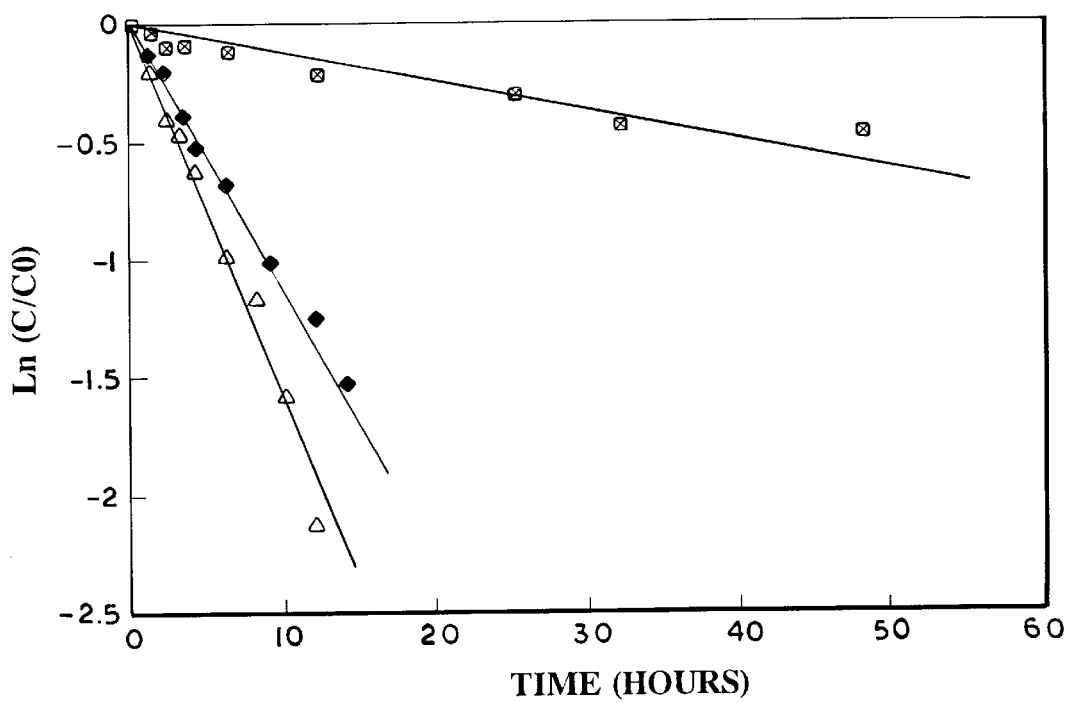
FIG. 14 is graph comparing TNT reduction kinetics in aquifer material after incubation with a protein extract containing a TNT reducing agent. The x-containing open square symbol represents TNT in aquifer material alone. The $t_{1/2}$ is 70.6 hours. The x-containing open diamond symbol represents TNT plus protein extract. The $t_{1/2}$ is 6.5 hours. The x-containing open triangle symbol represents TNT in aquifer material plus protein extract. The $t_{1/2}$ is 4.2 hours.

FIG. 14 shows the kinetics of TNT degradation in the three systems described above. When Ln(c/c0) was plotted as a function of time, the regression analysis showed that the reaction of TNT follows first-order kinetics in all three systems. A comparison of these three results indicates that the protein extract bound to sediment enhances the rate of disappearance of TNT. Half-life of TNT in the combined aquifer material and protein extract system is smaller than that in protein extract system alone.

Figure 15:
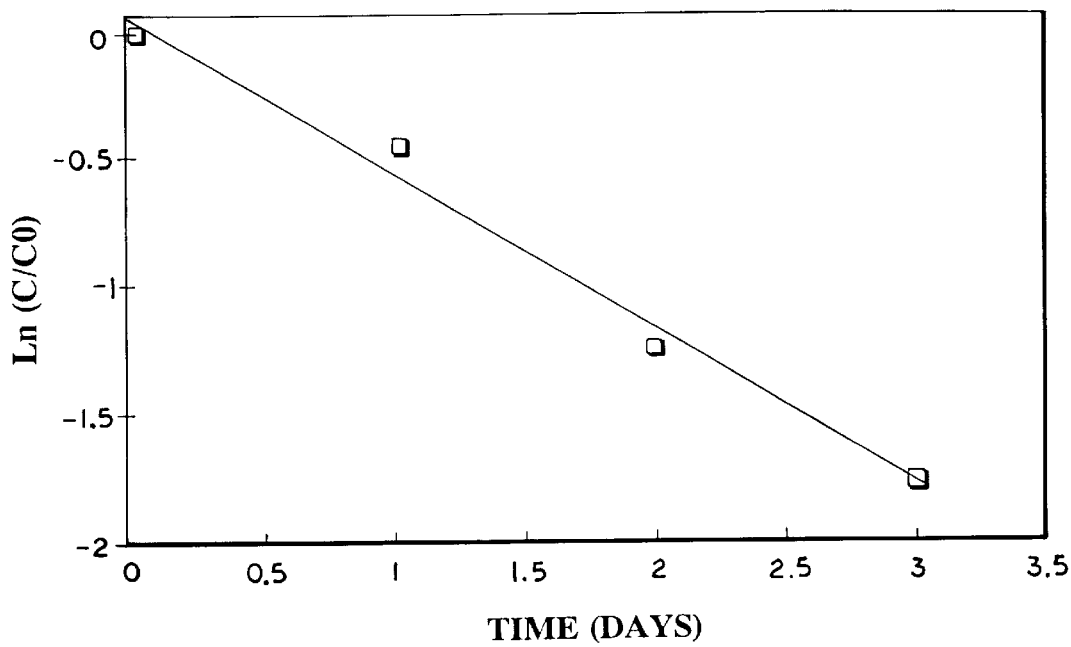
FIG. 15 is a graph showing the reduction of 1.6 ppm TNT in an aqueous solution of 1% iron (w/v) in the absence of reducing agent. The $t_{1/2}$ is 1.14 days and $r^2$=0.99.

The effects of the addition of iron to the system was analyzed. 1.6 ppm TNT in distilled water was combined with 1% (w/v) iron powder under anaerobic conditions. As shown in FIG. 15, a plot of ln(c/c0) as a function of time using the regression method gave a straight line indicating that the TNT reduction is a first order process with a half-life of 1.14 days. The TNT reduction rate was increased by shaking the reactor to enhance the mass transfer. It should be noted that TNT reduced products were not observed in this study, most likely because the reaction rate of TNT reduced products on the metal surface was extremely fast.

Figure 16:
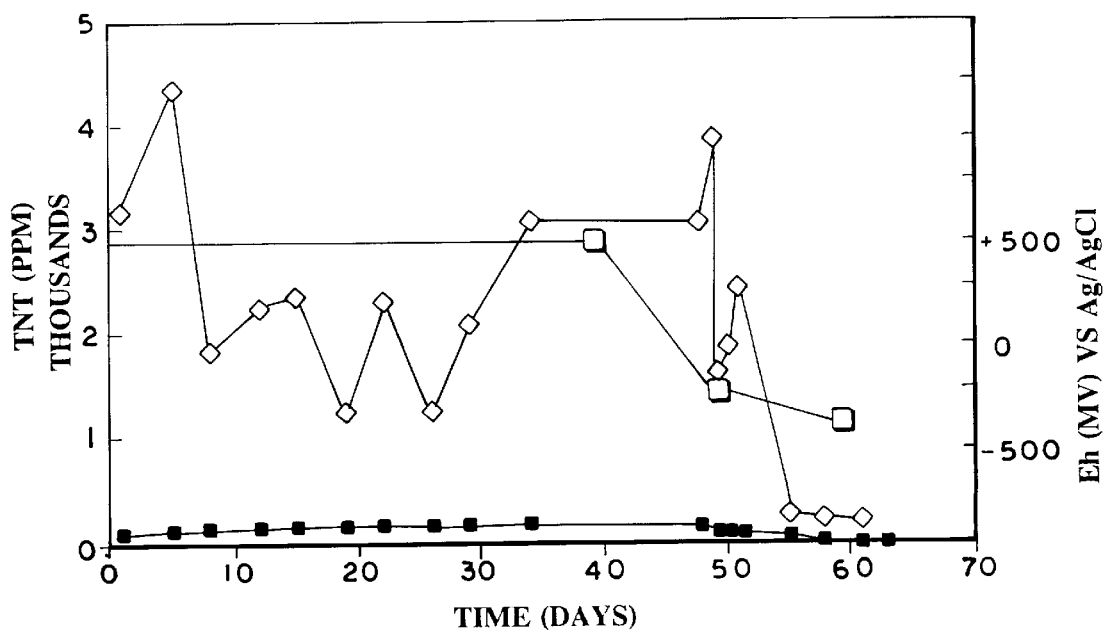
FIG. 16 is a graph showing TNT reduction in flooded contaminated soil samples. The first arrow indicates that iron was added after 48 days, and the second arrow indicates that the sample was inverted to mix the contents after 51 days. The solid square represents supernatant. The open triangle represents sediment. The open square represents Eh.

A bench scale experiment was designed to investigate the redox degradation of TNT in contaminated soils. TNT contaminated soils were sampled from Alabama Army Ammunition Plant near Childersburg, Ala. 100 g of contaminated soil was flooded by water to a volume of 900 ml in a quart jar. At given time intervals, aliquots of 1–1.5 ml were taken from the reaction mixture and centrifuged. The supernatant was decanted and the sediment was extracted with acetonitrile. Both supernatant and sediment extracts were analyzed. FIG. 16 shows TNT concentration remaining in supernatant and solid phase as a function of time. The initial concentration of TNT in contaminated soil was 6000 ppm based on dry soil. In this study, the concentration of TNT remaining in the solid phase based on wet soil was determined. The concentration of TNT in both aqueous and solid phases were almost constant during 48 day period. Also, Eh measured in the glove box was very positive. At day 48, 9 grams of iron powder was added to the reaction system. Although the concentration of TNT in solid phase did not change significantly, both the concentration of TNT in supernatant and the Eh decreased with time. When the reaction jar was inverted and shaken vigorously, both TNT in the supernatant and solid phases decreased dramatically. Therefore mass transfer enhances the degradation of TNT.

Modifications and variations of the contaminant remediation method and reducing agent composition will be obvious to those skilled in the art from the foregoing description. Such modifications and variations are intended to come within the scope of the appended claims.

We claim:

1. A reducing agent for chemical reduction of an environmental contaminant comprising at least one isolated plant enzyme, the enzyme having a molecular weight greater than 5000 daltons and less than 650,000 daltons, wherein the enzyme is an enzyme of a common aquatic weed and has chemical reducing activity for remediation of an environmental contaminant selected from the group consisting of nitroorganics, halogenated hydrocarbons, cyano compounds, and anisoles, wherein the enzyme is not ribulose 1,5-biphosphate carboxylase/oxygenase.

2. The reducing agent of claim 1 wherein the enzyme is obtained from a sediment sample extract.

3. The reducing agent of claim 1 wherein the enzyme is an enzyme of the hornwort.

4. The reducing agent of claim 1 wherein the enzyme has subunits having a molecular weight selected from the group consisting of 19,000, 37,000, 66,000 and 150,000, and wherein one or more subunits combine to form an enzyme.

5. The reducing agent of claim 1 wherein the enzyme has a molecular weight of approximately 316,000 daltons and nitroorganic compound reducing activity.

6. The reducing agent of claim 5 wherein the enzyme has a molecular weight of approximately 316,000 daltons and 2,4,6, -trinitrotoluene (TNT) reducing activity.

7. The reducing agent of claim 1 wherein the enzyme has a molecular weight of approximately 600,000 daltons and nitroorganic compound reducing activity.

8. The reducing agent of claim 1 wherein the enzyme has a molecular weight of approximately 293,000 daltons and halogenated hydrocarbon reducing activity.

9. The reducing agent of claim 8 wherein the enzyme has a molecular weight of approximately 293,000 daltons and the ability to chemically reduce a halogenated hydrocarbon selected from the group consisting of hexachloroethane, tetrachloroethene, tetrabromoethene, and trichloroethene.

10. The reducing agent of claim 1 in combination with a contaminated environmental material selected from the group consisting of soil, sediment, water and aquifer material.

* * * * *